US012090059B2

(12) United States Patent
Berry

(10) Patent No.: US 12,090,059 B2
(45) Date of Patent: Sep. 17, 2024

(54) INTERLOCKING SPINAL DISC PROSTHETIC

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 26 days.

(21) Appl. No.: 17/150,924

(22) Filed: Jan. 15, 2021

(65) Prior Publication Data

US 2021/0275320 A1    Sep. 9, 2021

Related U.S. Application Data

(63) Continuation-in-part of application No. 16/810,217, filed on Mar. 5, 2020, now Pat. No. 11,291,553.

(51) Int. Cl.
*A61F 2/44* (2006.01)
*A61F 2/30* (2006.01)

(52) U.S. Cl.
CPC .. *A61F 2/4425* (2013.01); *A61F 2002/30069* (2013.01); *A61F 2002/30079* (2013.01); *A61F 2002/30131* (2013.01); *A61F 2002/30433* (2013.01); *A61F 2002/30593* (2013.01); *A61F 2002/30632* (2013.01)

(58) Field of Classification Search
None
See application file for complete search history.

(56) References Cited

U.S. PATENT DOCUMENTS

| 7,905,921 B2* | 3/2011 | Kim | A61F 2/4425 |
| | | | 623/17.15 |
| 8,083,800 B2* | 12/2011 | Edie | A61F 2/44 |
| | | | 623/17.12 |
| 9,408,714 B1 | 8/2016 | Whipple | |
| 2003/0135277 A1* | 7/2003 | Bryan | A61B 17/1671 |
| | | | 623/17.13 |
| 2005/0165485 A1* | 7/2005 | Trieu | A61F 2/442 |
| | | | 623/17.13 |
| 2005/0165486 A1* | 7/2005 | Trieu | A61F 2/442 |
| | | | 623/17.13 |
| 2005/0187631 A1* | 8/2005 | Van Hoeck | A61F 2/442 |
| | | | 623/17.13 |
| 2005/0203626 A1* | 9/2005 | Sears | A61F 2/4425 |
| | | | 623/17.11 |
| 2006/0135277 A1* | 6/2006 | Marnocha | A63B 69/3614 |
| | | | 473/220 |
| 2007/0010826 A1 | 1/2007 | Rhoda et al. | |

(Continued)

FOREIGN PATENT DOCUMENTS

EP    3597154 A1    1/2020

OTHER PUBLICATIONS

Extended European Search Report for EP Application No. 21160419 dated Aug. 10, 2021.
(Continued)

*Primary Examiner* — Tessa M Matthews
(74) *Attorney, Agent, or Firm* — McCarter & English, LLP; James M. Smedley; Alex Korona

(57) ABSTRACT

The present invention relates generally to a prosthetic spinal disc for replacing a damaged or degenerated disc between two vertebrae of a spine. The present invention also relates to prosthetic spinal disc designs that have either or both interlocking and magnetic components.

16 Claims, 29 Drawing Sheets

(56) References Cited

U.S. PATENT DOCUMENTS

| | | |
|---|---|---|
| 2007/0168032 A1 | 7/2007 | Muhanna et al. |
| 2007/0191958 A1 | 8/2007 | Abdou |
| 2007/0233251 A1 | 10/2007 | Abdou |
| 2008/0033554 A1* | 2/2008 | Lechmann ............ A61F 2/4425 623/17.14 |
| 2009/0043391 A1 | 2/2009 | de Villiers et al. |
| 2010/0114319 A1* | 5/2010 | Edie ........................ A61F 2/44 623/17.12 |
| 2014/0277469 A1 | 9/2014 | Baynham |

OTHER PUBLICATIONS

European Examination Report, dated Jun. 25, 2024, issued in corresponding European Patent Application No. 21160419.4.

* cited by examiner

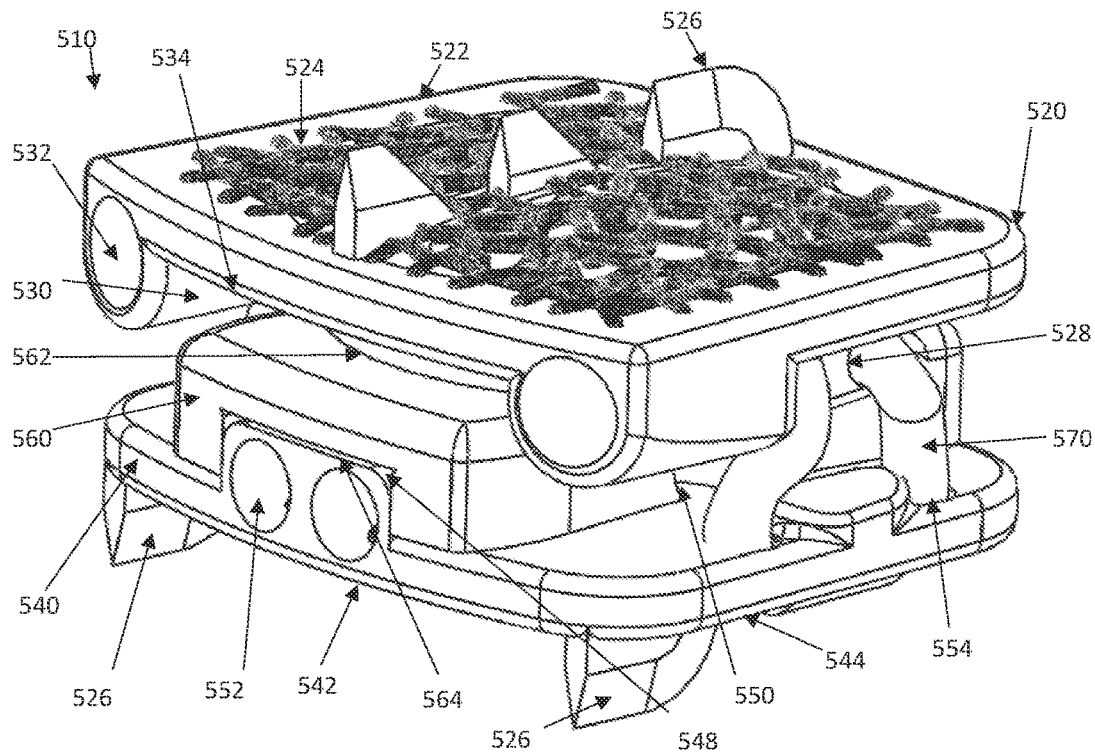
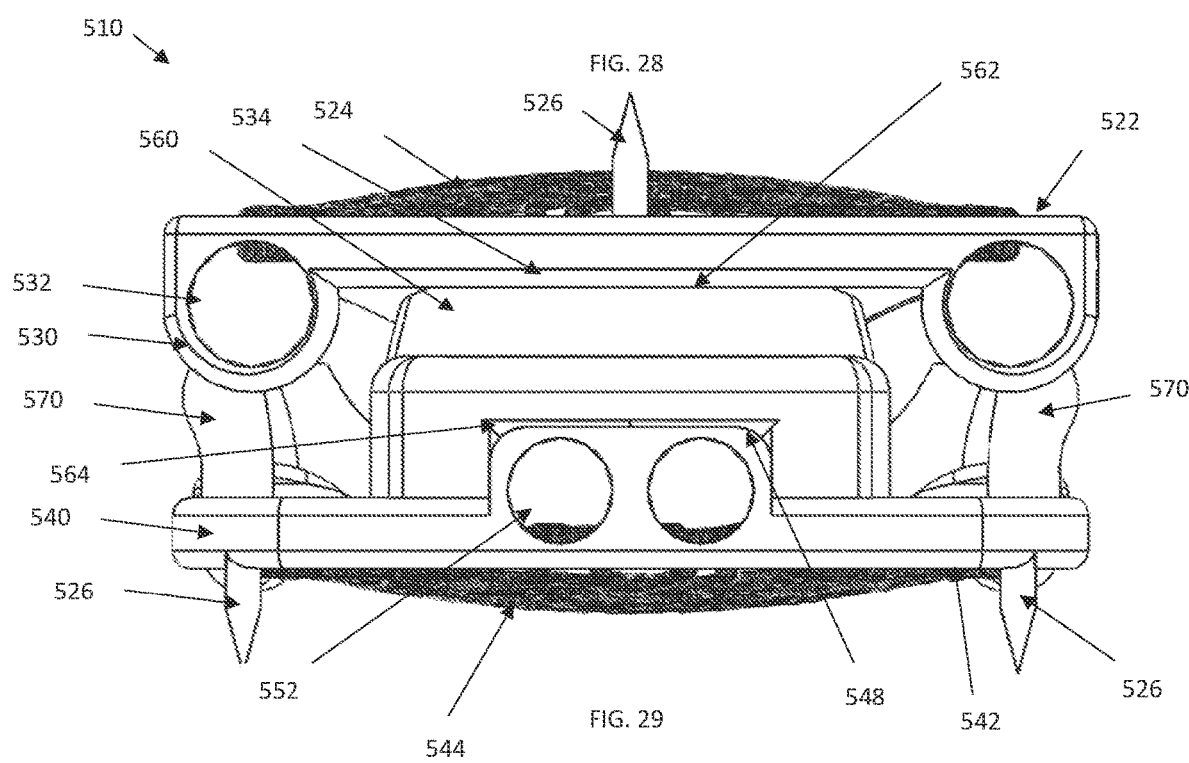
FIG. 29

INTERLOCKING SPINAL DISC PROSTHETIC

FIELD OF THE INVENTION

The present invention relates to a prosthetic spinal disc for fully or partially replacing a damaged or degenerated disc between two vertebrae of a spine. The present invention also relates to prosthetic spinal disc designs that have either or both interlocking and magnetic components.

CROSS-REFERENCE TO RELATED APPLICATIONS

This application is a continuation-in-part and claims the benefit of U.S. patent application Ser. No. 16/810,217 filed on Mar. 5, 2020, the entire disclosure of which is incorporated herein by reference.

BACKGROUND OF THE INVENTION

The present disclosure relates generally to prosthetic replacement devices, and more particularly, to artificial disc replacement devices comprising magnets.

Intervertebral discs are located between concave articular surfaces of the adjacent vertebral body endplates. The discs form an important and unique articulating system in the spine, allowing for multiplanar motion. In general, intervertebral discs permit movements such as flexion, extension, lateral flexion, and rotation as well as a cushion for axial compression.

Disc replacement devices have been used to repair and/or replace injured or damaged intervertebral discs. However, previous disc replacement devices possess a number of disadvantages. For example, to enable movement, some disc replacement devices contain mobile parts and to implant such a device, extensive disc space preparation is required. In some scenarios, once implanted, the device may wear against adjacent vertebral bodies or itself and generate debris in the disc space. As a result, an implanted disc may fail to function properly. Such debris may also damage the surrounding tissue. Additionally, these disc replacements offer little cushioning for axial loads. Excessive shock to the spine column caused by lack of cushioning can damage other, previously healthy, portions of the spine.

Other disc replacement devices have eliminated mobile parts by utilizing liquids or gels to produce or facilitate motion. While these liquids and gels may provide cushioning for axial loads, these substances often have a very limited range of motion in regards to flexion, extension, lateral flexion and rotation. Additionally, such liquids or gels must be properly contained, and their leakage may cause unwanted results or outcomes.

Accordingly, there is a need in the art for a disc replacement device with a means of preventing or reducing wear debris and providing shock absorption to replace the natural shock absorption of the disc being replaced. The present invention is provided to solve the problems discussed above and other problems, and to provide advantages and features not provided by existing disc replacement devices. The advantages of the present invention will be explained and will become obvious to one skilled in the art through the summary, descriptions, and drawings of the invention that follow.

SUMMARY OF INVENTION

The present invention relates generally to a prosthetic spinal disc for replacing a damaged or degenerated disc between two vertebrae of a spine. In particular, the present invention encompasses a prosthetic spinal disc with articulation facilitating components.

In accordance with embodiments of the present invention, an intervertebral prosthetic disc may comprise two endplate components, for example, upper and lower endplate components, each endplate component having a magnetic portion. In any embodiment, the magnetic portion may be comprised of one or more magnet components. In accordance with an exemplary embodiment of the present invention, a first endplate component may be configured with a magnetic portion adapted to repel the magnetic portion of a second endplate component. The repelling of the magnetic portions of the two endplate components may enable the first endplate component to articulate about the second endplate component. In some embodiments, one or more connector components may be configured to connect the upper endplate component to the lower endplate component.

In accordance with embodiments of the present invention, the magnetic portion of the endplate components may be configured to either completely or substantially prevent the two endplate components from coming into direct contact with one another. This reduction or lack of contact between the two endplate components may substantially reduce or altogether prevent the generation of wear debris that may otherwise be problematic if the two endplate components were to rub against or otherwise come into contact with one another. Such a configuration may also prevent wear debris from impairing, damaging or adversely affecting the device, surrounding tissue, or nearby bone. Additionally, the magnetic portions of the endplate components may cause the two endplate components to repel one another such that a cushioning effect is generated in the spine, to mimic the movement of a natural disc.

In accordance with embodiments of the present invention, the magnetic portions of each of the endplate components may be configured to repel as well as contain the magnetic portion of the other endplate component. For example, a magnetic portion of a first endplate component may be configured to repel and contain a magnetic portion of a second endplate component. In some examples, the magnetic portion of the first endplate component may be oriented in a generally exterior position to that of the magnetic portion of the second endplate component. Such a configuration may enable the first endplate component to articulate about the second endplate component while containing the second endplate component within a chosen or desired area.

BRIEF DESCRIPTION OF THE DRAWINGS

FIG. 28 is a perspective view of a prosthetic spinal disc in accordance with a sixth embodiment of the present invention.

FIG. 29 is an anterior view of a prosthetic spinal disc in accordance with a sixth embodiment of the present invention.

DETAILED DESCRIPTION OF ILLUSTRATIVE EMBODIMENTS

In the Summary above and in this Detailed Description, and the claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

In accordance with embodiments of the present invention, the prosthetic spinal disc disclosed herein may be configured to be implanted into a spine, to imitate the functions of a healthy spinal disc, for example, by providing and permitting the same mobility and load carrying ability of a healthy spinal disc. In particular, embodiments of present invention are directed towards prosthetic spinal discs comprising articulation facilitating components configured to prevent or reduce wear debris and provide shock absorption to replace the natural shock absorption of the spinal disc being replaced.

First Exemplary Embodiment

Figure 1:
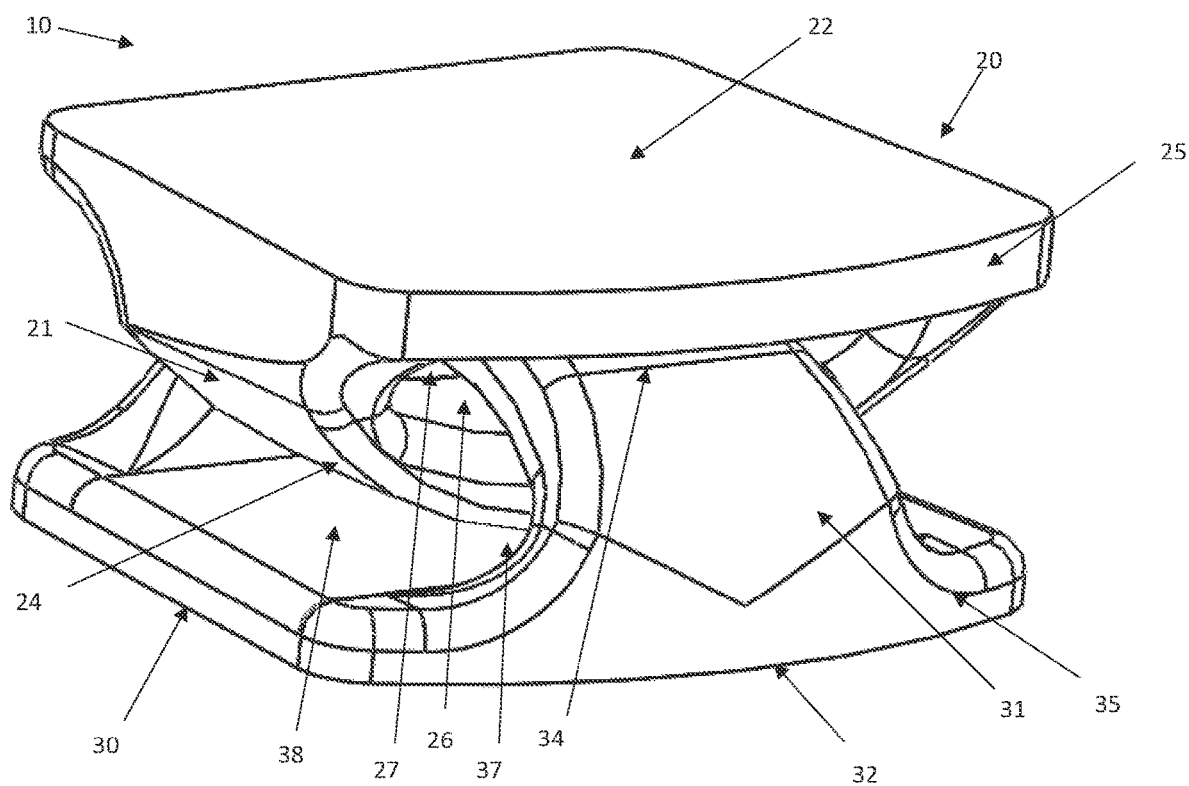
FIG. 1 is a perspective view of a prosthetic spinal disc in accordance with a first embodiment of the present invention.

FIG. 1 depicts a perspective view of a prosthetic spinal disc in accordance with an embodiment of the present invention. In FIG. 1, the prosthetic spinal disc 10 comprises a first endplate component 20 and a second endplate component 30. In the illustrated example, the first endplate component 20 is comprised of a first base 25 and a first u-shaped element 21. In some embodiments, the first endplate component 20 may comprise a magnetic portion. In some embodiments, the magnetic portion may be disposed on or within the first base component 25. In the depicted example, the second endplate component 30 includes a second base 35 and a second u-shaped element 31. In some embodiments, the second endplate component 30 may comprise a magnetic portion. In some embodiments, the magnetic portion may be disposed on or within the second base component 35. In some embodiments, the u-shaped elements 21 and 31 may be formed of a resilient material. In some embodiments, the u-shaped elements 21 and 31 may be flexible. In the illustrated example, an exterior portion of the first endplate component 20 includes a vertebral mating surface 22. In the depicted example, an exterior portion of the second endplate component 30 includes a vertebral mating surface 32. The first base 25 and the second base 35 are contemplated to have the orientation of any geometric shape, including: squares, rectangles, circles, ovals, pentagons, hexagons, triangles. One of ordinary skill in the art would appreciate that there are numerous suitable and advantageous arrangements for the geometric orientation of the first and second bases depending on the specific intended use application of the particular prosthetic spinal disc and embodiments of the present invention are contemplated for use with any such prosthetic spinal disc arrangements.

Figure 2:
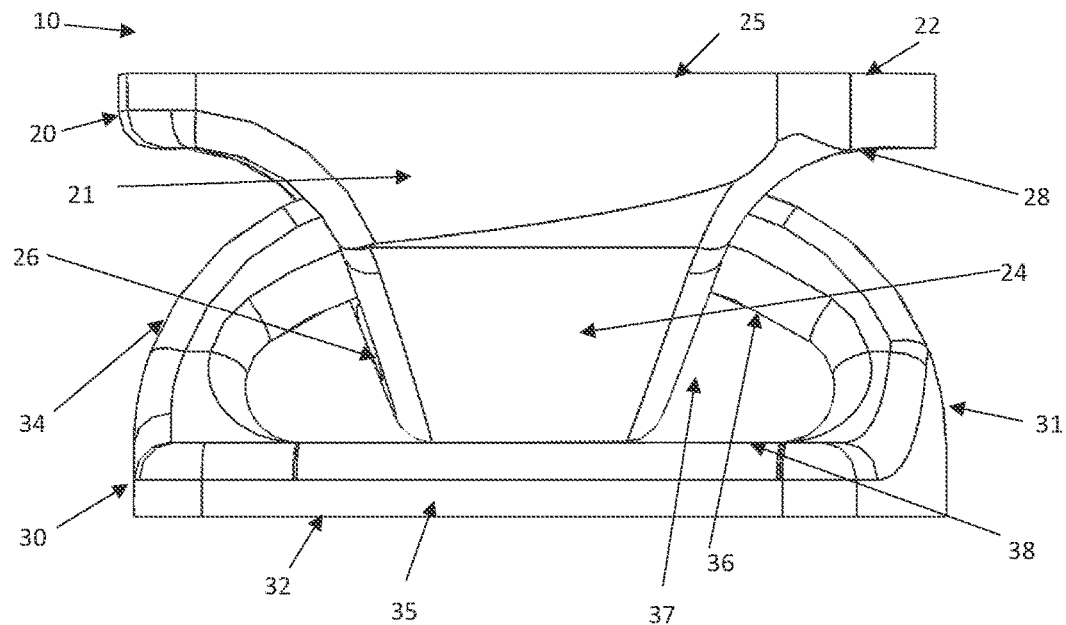
FIG. 2 is lateral view of a prosthetic spinal disc in accordance with a first embodiment of the present invention.

FIG. 2 depicts a lateral view of a prosthetic spinal disc in accordance with an embodiment of the present invention. In the depicted example, the first endplate component 20 includes a first base 25 having a base articulation surface 28 and a magnetic portion on or near an interior surface thereof and a vertebral mating surface 22 on an exterior surface thereof. In some embodiments, the base articulation surface 28 is flat. In some embodiments, the base articulation surface 28 is concave. In an illustrative example, the base articulation surface 28 permits the articulation or movement of the second u-shaped element 31 against the first base 25. In the illustrated example, a u-shaped element 21 comprising an exterior articulating surface 24 and an interior articulating surface 26 extends from the first base 25. In some embodiments, the u-shaped element 21 extends from the base articulation surface 28. In the depicted example, the exterior articulating surface 24 is generally convex. In the illustrated example, the interior articulating surface 26 is generally concave. In the depicted example, the u-shaped element 21 of the first endplate component 20 extends from one side of the base 25 to a second side of the base 25. In the depicted example, disposed between the u-shaped element 21 and the base 25 is an aperture 27 configured to receive a second u-shaped element 31. In the illustrated example, the second endplate component 30 includes a second base 35 having a base articulation surface 38 and a magnetic portion on or near an interior surface thereof and vertebral mating surface 32 on an exterior surface thereof. In some embodiments, the base articulation surface 38 is flat. In some embodiments, the base articulation surface 38 is concave. In the illustrated example, the second u-shaped element 31 comprising an exterior articulating surface 34 and an interior articulating surface 36 extends from the second base 35. In some embodiments, the u-shaped element 31 extends from the base articulation surface 38. In the depicted example, the exterior articulating surface 34 is generally convex. In the illustrated example, the interior articulating surface 36 is generally concave. In the depicted example, the u-shaped element 31 of the second endplate component 30 extends from one side of the base 35 to a second side of the base 35. In the depicted example, disposed between the u-shaped element 31 and the second base 35 is an aperture 37 configured to receive the u-shaped element 21. In the illustrated example, a portion of the first u-shaped element 21 is received within the aperture 37 of the u-shaped element 31 and a portion of the u-shaped element 31 is received within the aperture 27 of the u-shaped element 21, interlocking the first u-shaped element 21 with the second u-shaped element 31.

Figure 3:
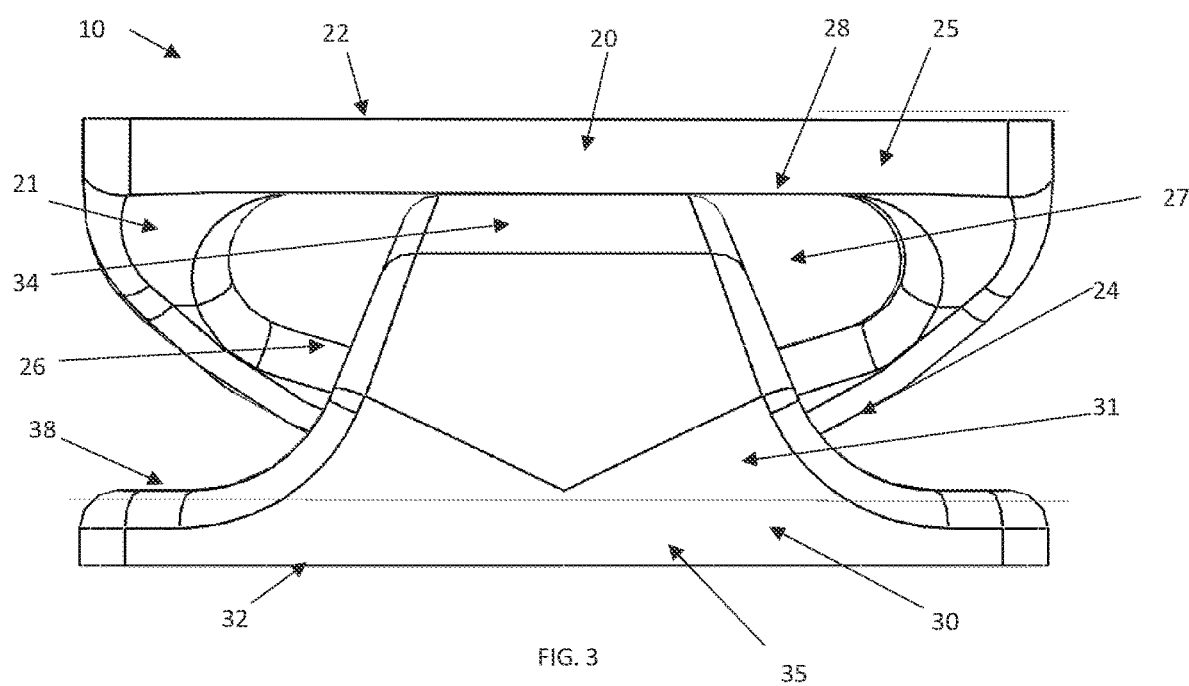
FIG. 3 is an anterior view of a prosthetic spinal disc in accordance with a first embodiment of the present invention.

FIG. 3 depicts an anterior view of a prosthetic spinal disc in accordance with an embodiment of the present invention. In the depicted example, the interior surface of the first endplate component 20 includes the base articulation surface 28. In the illustrated example, the u-shaped element 21 extends from the base articulation surface 28. In the depicted example, the interior surface of the second endplate component 30 includes the base articulation surface 38. In the illustrated example, the u-shaped element 31 extends from the base articulation surface 38. As shown in the depicted example, the first u-shaped element 21 is interlocked with the second u-shaped element 31. In the depicted example, the exterior articulating surface 24 of the first u-shaped element 21 rests on the base articulation surface 38 of the second endplate component 30. In the illustrated example, the exterior articulating surface 24 of the first u-shaped element 21 is configured to articulate on the base articulation surface 38 of the second endplate component 30. Similarly, in the depicted example, the base articulation surface 28 of the first endplate component 20 rests on the exterior articulating surface 34 of the second u-shaped element 31. Moreover, in the illustrated example, the exterior articulating surface 34 of the second endplate component 30 is configured to articulate on the base articulation surface 28 of the first endplate component 20.

In any embodiment, the u-shaped elements 21 and 31 may be substantially round. In some embodiments, the u-shaped elements 21 and 31 may have substantially oval profiles. In some embodiments, the u-shaped elements may include edges. In some embodiments, the u-shaped elements may be substantially square. One of ordinary skill in the art would appreciate that there are numerous suitable and advantageous arrangements for the u-shaped elements depending on the specific intended use application of the particular prosthetic spinal disc and embodiments of the present invention are contemplated for use with any such prosthetic spinal disc arrangements.

Figure 4:
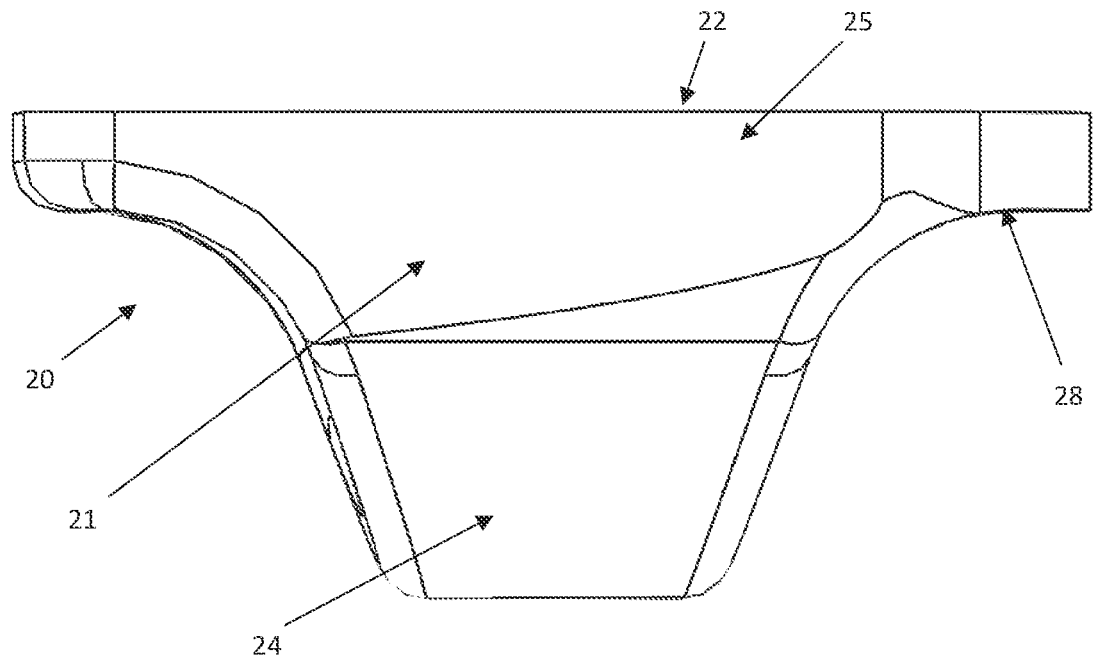
FIG. 4 is a lateral view of a first endplate component of a prosthetic spinal disc in accordance with a first embodiment of the present invention.
Figure 5:
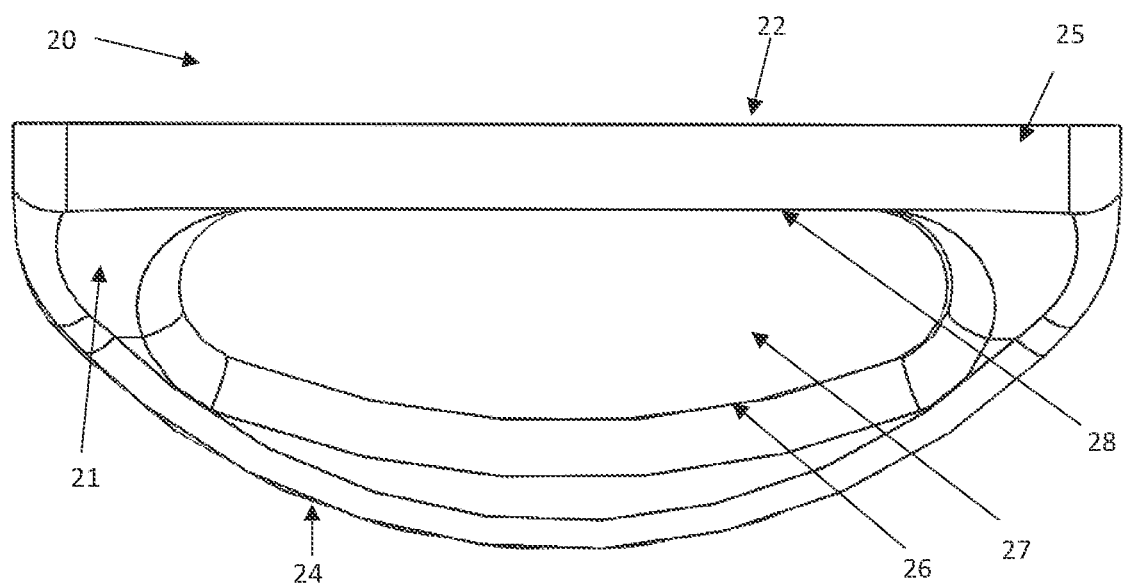
FIG. 5 is an anterior view of a first endplate component of a prosthetic spinal disc in accordance with a first embodiment of the present invention.

FIGS. 4 and 5 depict lateral and anterior views of a first endplate component of a prosthetic spinal disc in accordance with a first embodiment of the present invention. In the depicted examples, the first endplate component 20 includes a vertebral mating surface 22 on a top side, opposing a base articulation surface 28 on a bottom side. In the illustrated embodiment, the u-shaped element 21 extends from the interior surface of the first base 25. In the depicted embodiment, the u-shaped element 21 connects with the interior surface of the first base 25 at least at two points. In the illustrated example, an aperture 27 disposed between the first base 25 and the first u-shaped element 21 is configured to receive the second u-shaped element 31.

Figure 6:
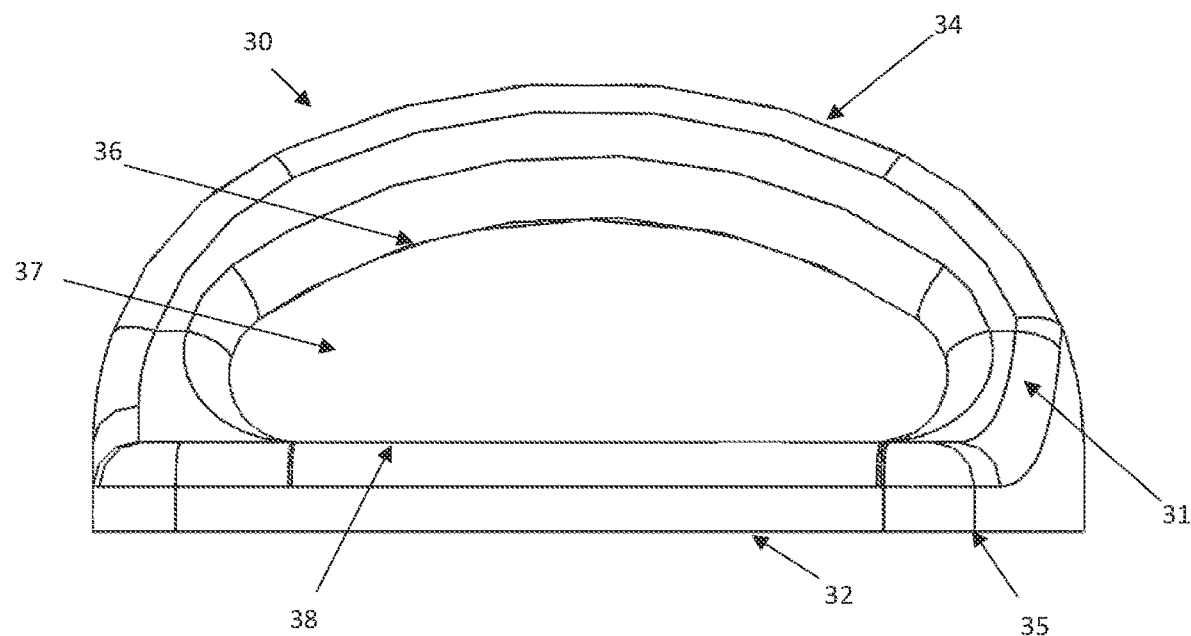
FIG. 6 is a lateral view of a second endplate component of a prosthetic spinal disc in accordance with a first embodiment of the present invention
Figure 7:
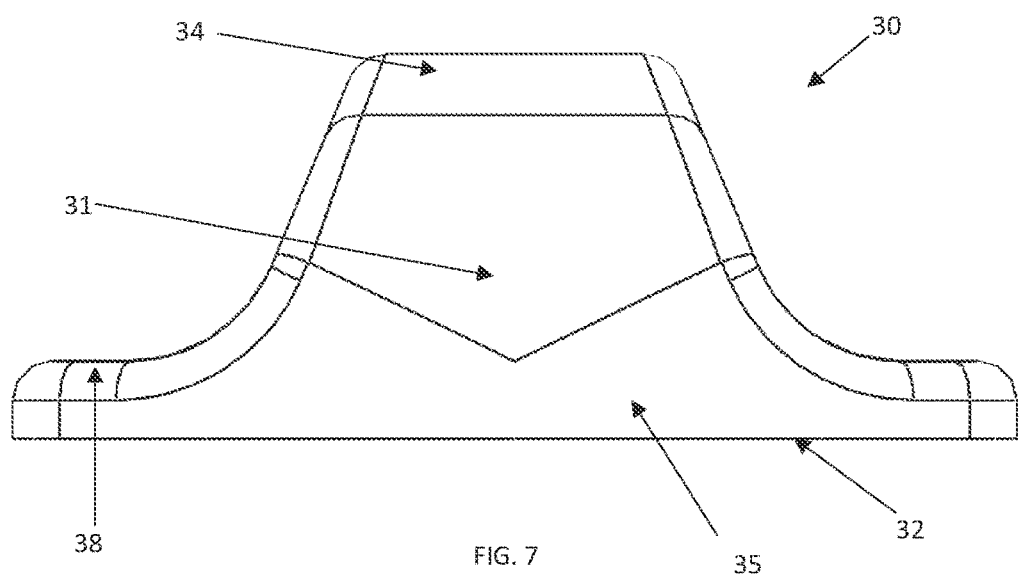
FIG. 7 is an anterior view of a second endplate component of a prosthetic spinal disc in accordance with a first embodiment of the present invention.

FIGS. 6 and 7 depict lateral and anterior views of a second endplate component of a prosthetic spinal disc in accordance with a first embodiment of the present invention. In the depicted example, the second endplate component 30 includes a vertebral mating surface 32 on a top side, opposing a base articulation surface 38 on a bottom side. In the illustrated embodiment, the u-shaped element 31 extends from the interior surface of the second base 35. In the depicted embodiment, the u-shaped element 31 connects with the interior surface of the second base 36 at least at two points. In the illustrated example, an aperture 37 disposed between the second base 35 and the second u-shaped element 31 is configured to receive the first u-shaped element 21.

Figure 8:
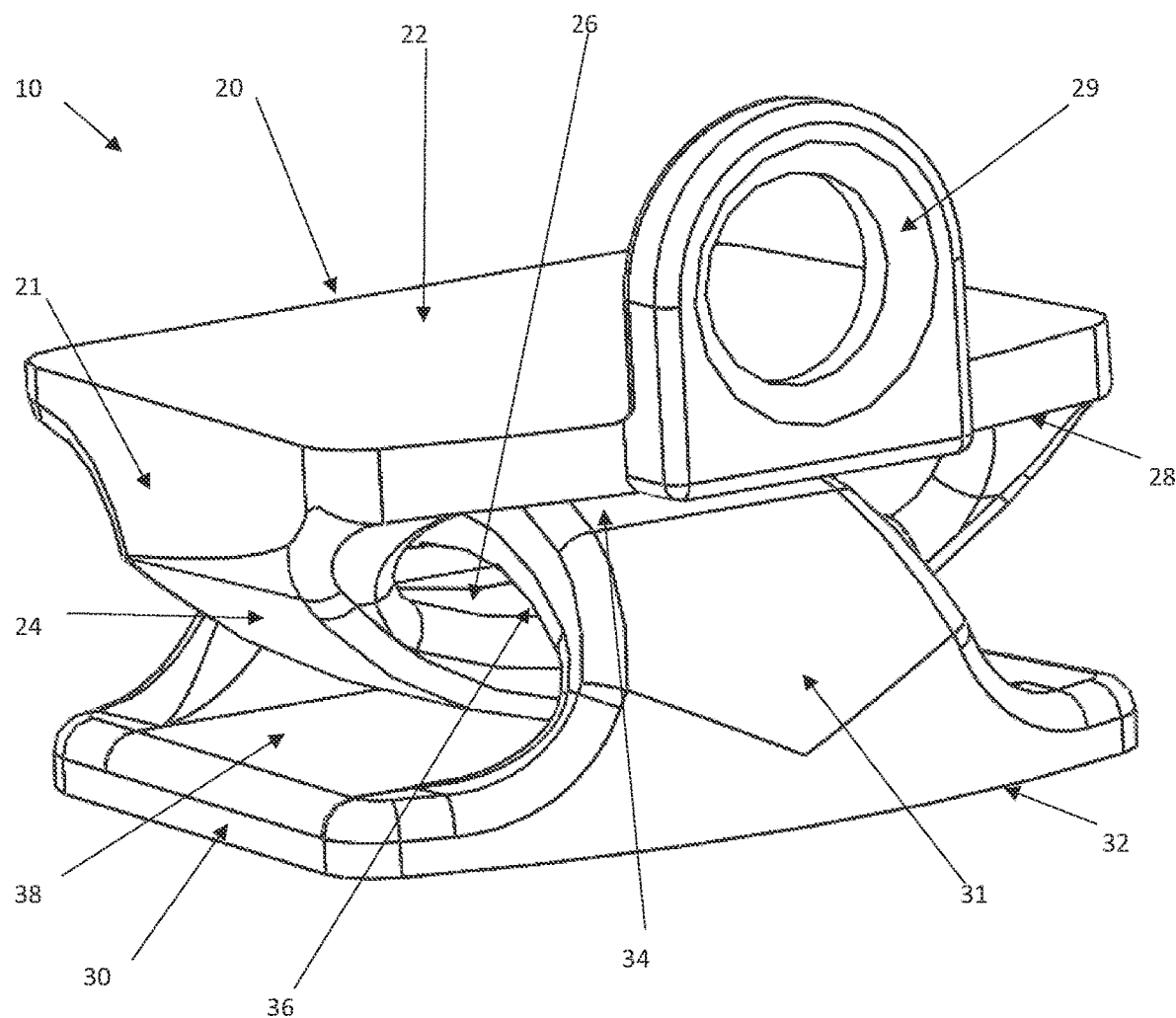
FIG. 8 is a perspective view of a prosthetic spinal disc with a fastening aperture in accordance with a first embodiment of the present invention.

FIG. 8 depicts a perspective view of a prosthetic spinal disc with a fastening aperture in accordance with a first embodiment of the present invention. In the depicted example, the prosthetic spinal disc 10 comprises a first endplate component 20 and a second endplate component 30. In the depicted example, the first endplate component 20 includes a first base 25 having a base articulation surface 28 on an interior surface thereof and a vertebral mating surface 22 on an exterior surface thereof. In the illustrated example, a u-shaped element 21 comprising an exterior articulating surface 24 and an interior articulating surface 26 extends from the interior surface of the first base 25. In the depicted example, the exterior articulating surface 24 is generally convex. In the illustrated example, the interior articulating surface 26 is generally concave. In the depicted example, the u-shaped element 21 of the first endplate component 20 extends from one side of the first base 25 to a second side of the base 25. In the illustrated example, the second endplate component 30 includes a second base 35 having a base articulation surface 38 on an interior surface thereof and vertebral mating surface 32 on an exterior surface thereof. In any embodiment, the vertebral mating surfaces 22 and 32 may include spikes, teeth or porous areas to connect or secure the implant 10 to vertebral bodies. In the depicted example, a u-shaped element 31 comprising an exterior articulating surface 34 and an interior articulating surface 36 extends from the interior surface of the second base 35. In the depicted example, the exterior articulating surface 34 is generally convex. In the illustrated example, the interior articulating surface 36 is generally concave. In the depicted example, the u-shaped element 31 of the second endplate component 20 extends from one side of the second base 35 to a second side of the base 35. In the illustrated example, the first endplate component 20 includes a fastening aperture 29. In the depicted example, the fastening aperture 29 extends from the first base 25. In some embodiments, the second base includes a fastening aperture 29. In some embodiments, either or both of the first base 25 and the second base 35 include one or more fastening apertures 29. In some embodiments, the fastening aperture 29 is configured to receive a fastener (not shown). In any embodiment, the fastener may be a screw, pin or similar fastening member. In accordance with various embodiments, the fastener (not shown) may be inserted through the fastening aperture 29 to engage with a vertebral body, thereby securing the first endplate component 20 to the vertebral body.

Figure 9:
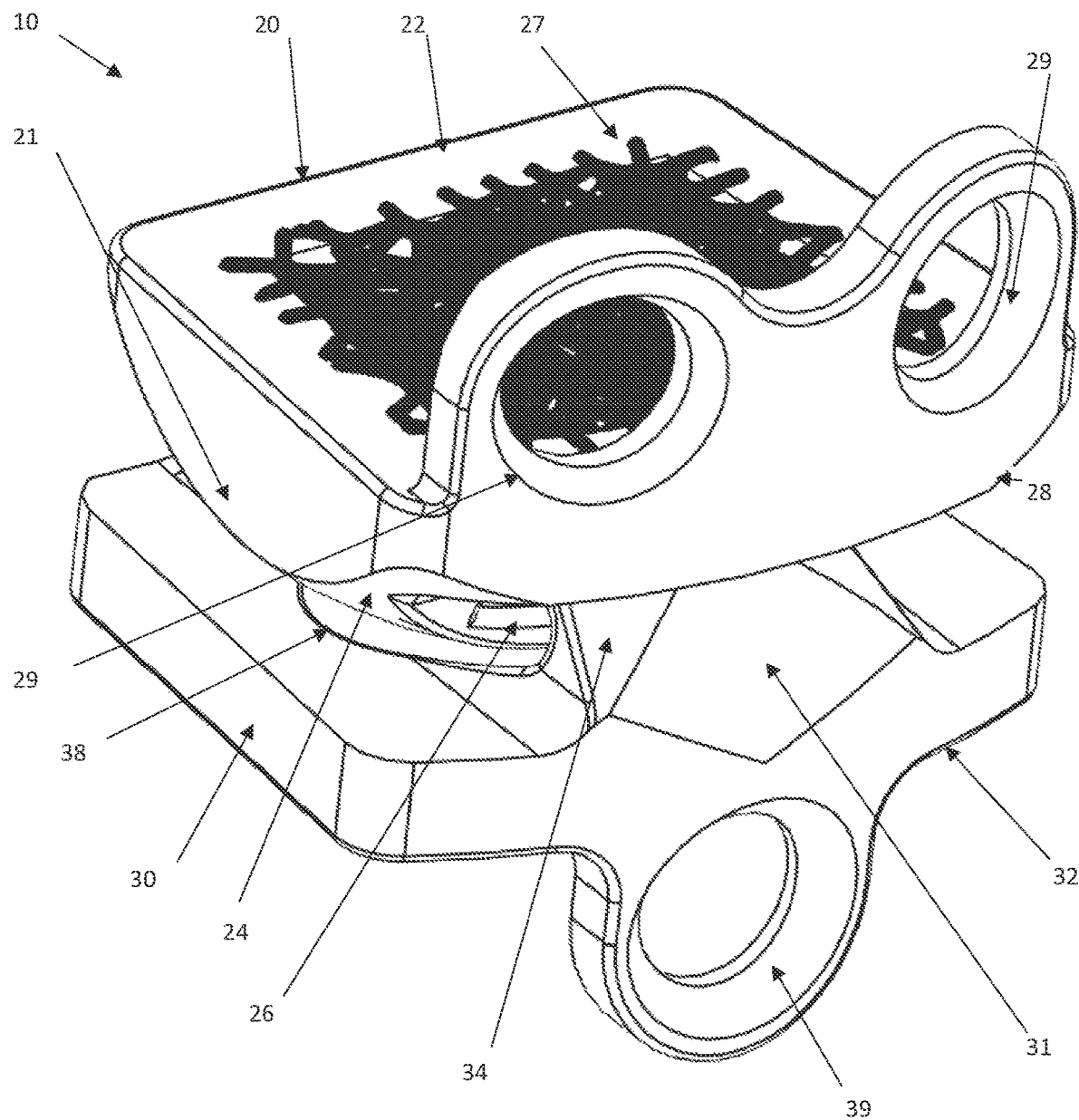
FIG. 9 depicts a perspective view of a prosthetic spinal disc configured with a porous bony ingrowth region and a plurality of fastening apertures in accordance with a first embodiment of the present invention.

FIG. 9 depicts a perspective view of a prosthetic spinal disc configured with a porous bony ingrowth region and fastening apertures in accordance with a first embodiment of the present invention. In the depicted example, the prosthetic spinal disc 10 is comprised of a first endplate component 20 and a second endplate component 30. In the depicted example, the first endplate component 20 includes a first base 25 having a base articulation surface 28 on an interior surface thereof and a vertebral mating surface 22 on an exterior surface thereof. In the illustrated example, a porous bone ingrowth surface 50 is located on the vertebral mating surface 22. In any embodiment, the porous bone ingrowth surface 50 is configured to promote bony ingrowth. In some embodiments, the porous bone ingrowth surface 50 is an osteoconductive material. In any embodiment, the porous bone ingrowth surface 50 may have a porous or macrotexture surface to promote bone growth. In the illustrated example, a u-shaped element 21 comprising an exterior articulating surface 24 and an interior articulating surface 26 extends from the first base 25. In the depicted example, the exterior articulating surface 24 is generally convex. In the illustrated example, the interior articulating surface 26 is generally concave. In the depicted example, the u-shaped element 21 of the first endplate component 20 extends from one side of the first base to a second side of the first base 25. In the illustrated example, the second endplate component 30 includes a second base 35 having a base articulation surface 38 on an interior surface thereof and a vertebral mating surface 32 on an exterior surface thereof. In the depicted example, a u-shaped element 31 comprising an exterior articulating surface 34 and an interior articulating surface 36 extends from the second base 35. In the depicted example, the exterior articulating surface 34 is generally convex. In the illustrated example, the interior articulating surface 36 is generally concave. In the depicted example, the u-shaped element 31 of the second endplate component 20 extends from one side of the second base 35 to a second side of the second base 35. In the illustrated example, the first endplate component 20 and the second endplate component 30 each include fastening apertures 29. In any embodiment, one or more fastening apertures may be disposed on either or both of the first and second endplate components 20 and 30. The fastening apertures 29 may be configured to receive and engage with a fastener (not shown) in order to secure the prosthetic disc 10 to bone. In accordance with various embodiments, the fastener (not shown) may be inserted through the aperture 39 to engage with a vertebral body, thereby securing the second endplate component 30 to the vertebral body.

In any embodiment, the prosthetic spinal disc 10 and/or any components thereof may be 3D printed. For example, the first endplate component 20 may be printed concurrently with the second endplate component 30. Various embodiment implementations may include the u-shaped element 21 of the first endplate component 20 and the u-shaped element 31 of the second endplate component 30 printed to be interlocking with one another.

In an example illustrative of the design and operation of various embodiment implementations, the interior articulating surface 26 of the first u-shaped element 21 is configured to link with the interior articulating surface 36 of the second u-shaped element 31. In an illustrative example, the interior articulating surface 26 of the first u-shaped element 21 is configured to articulate against the interior articulating surface 36 of the second u-shaped element 31. In various embodiments, the u-shaped element 21 of the first endplate component 20 and the u-shaped element 31 of the second endplate component 30 may interlock with one another to prevent the two components from separating.

In another example illustrative of the design and operation of various embodiment implementations, the interlocked u-shaped elements 21 and 31 may prevent over extension of the vertebral joint once the prosthetic spinal disc 10 is implanted. Moreover, the opposing orientation of the u-shaped element 21 and the u-shaped element 31 may prevent over-rotation of each of the first and second endplate components 20 and 30, respectively. In an illustrative example, the second u-shaped element 31 and the first u-shaped element 21 may be configured to rest against and limit the movement of one another as the prosthetic spinal disc 10 rotates with the joint.

In another example illustrative of the design and operation of various embodiment implementations, the magnetic portion of the first endplate component 20 and the magnetic portion of the second endplate component 30 may be configured to repel each other to prevent excess movement in the longitudinal or vertical axis once the prosthetic implant 10 is implanted. Accordingly, the opposing forces of the magnetic portions of the first and second endplate components 20 and 30 may be configured to absorb shock, similar to the natural shock absorption of a natural disc. The magnetic portions may also be configured to prevent excess compression, approximation and distraction, in turn, limiting or preventing the creation of wear debris between the first base 25 and the second base 35.

Second Exemplary Embodiment

Figure 10:
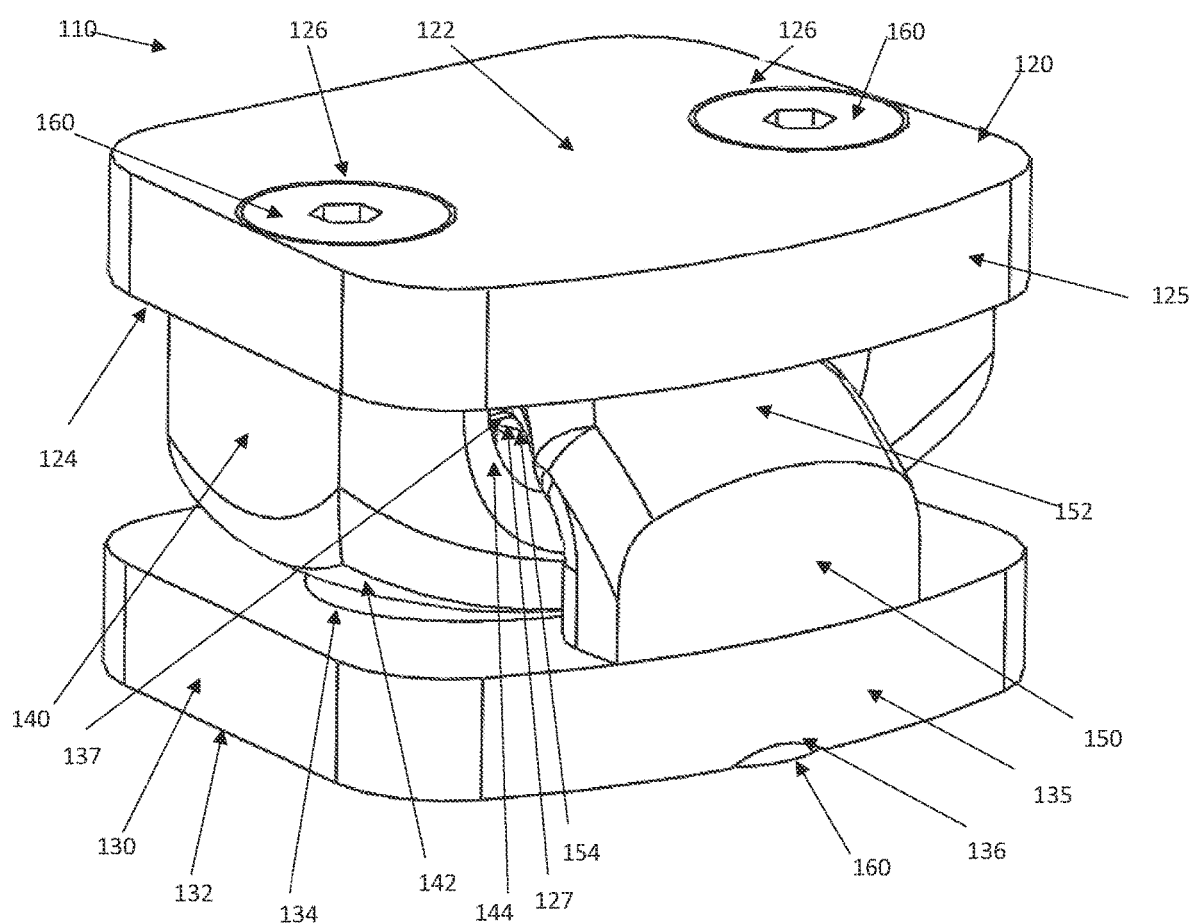
FIG. 10 is a perspective view of a prosthetic spinal disc in accordance with a second embodiment of the present invention.

FIG. 10 is a perspective view of a prosthetic spinal disc in accordance with a second embodiment of the present invention. In the depicted example, the prosthetic spinal disc 110 is comprised of a first endplate component 120 and a second endplate component 130. In some examples, each of the first and second endplate components 120 and 130 comprise a magnetic portion. In the illustrated example, a first u-shaped element 140 is connected to an interior portion of the first endplate component 120. Specifically, in the depicted example, the first u-shaped element 120 is connected an interior surface of a first base 125 of the first endplate component 120. Similarly, in the illustrated example, a second u-shaped element 150 is connected to the second endplate component 130. Specifically, in the depicted example, the second u-shaped element 150 is connected to an interior portion of a second base 135 of the second endplate component 130. In the depicted example, a first aperture 127 is disposed between the first u-shaped element 140 and the first base 125. In the illustrated example, the first aperture 127 is configured to receive and hold the second u-shaped element 150. Likewise, in the depicted example, a second aperture 137 is disposed between the second u-shaped element 150 and the second base 135. In the illustrated example, the second aperture 137 is configured to receive and hold the first u-shaped element 140. In the illustrated example, the first u-shaped element 140 is configured to articulate within the second aperture 137 and the second u-shaped element 150 is configured to articulate within the first aperture 127. In the depicted example, the first endplate component 120 includes a vertebral mating surface 22 on a top side, opposing a base articulation surface 124 on a bottom side. In some embodiments, the base articulation surface 124 is flat. In some embodiments, the base articulation surface 124 is concave.

In some embodiments, either or both of the first base 125 and the second base 135 include one or more fastening holes 126 for receiving fasteners 160 configured to secure the first u-shaped element 140 to the first base 125 and the second u-shaped element 150 to the second base 135. In any embodiment, the fasteners 160 may be screws, pins, or any similar fastening members. In the depicted example, the first u-shaped element 140 is fastened to the first base 125 by two fasteners 160.

Figure 11:
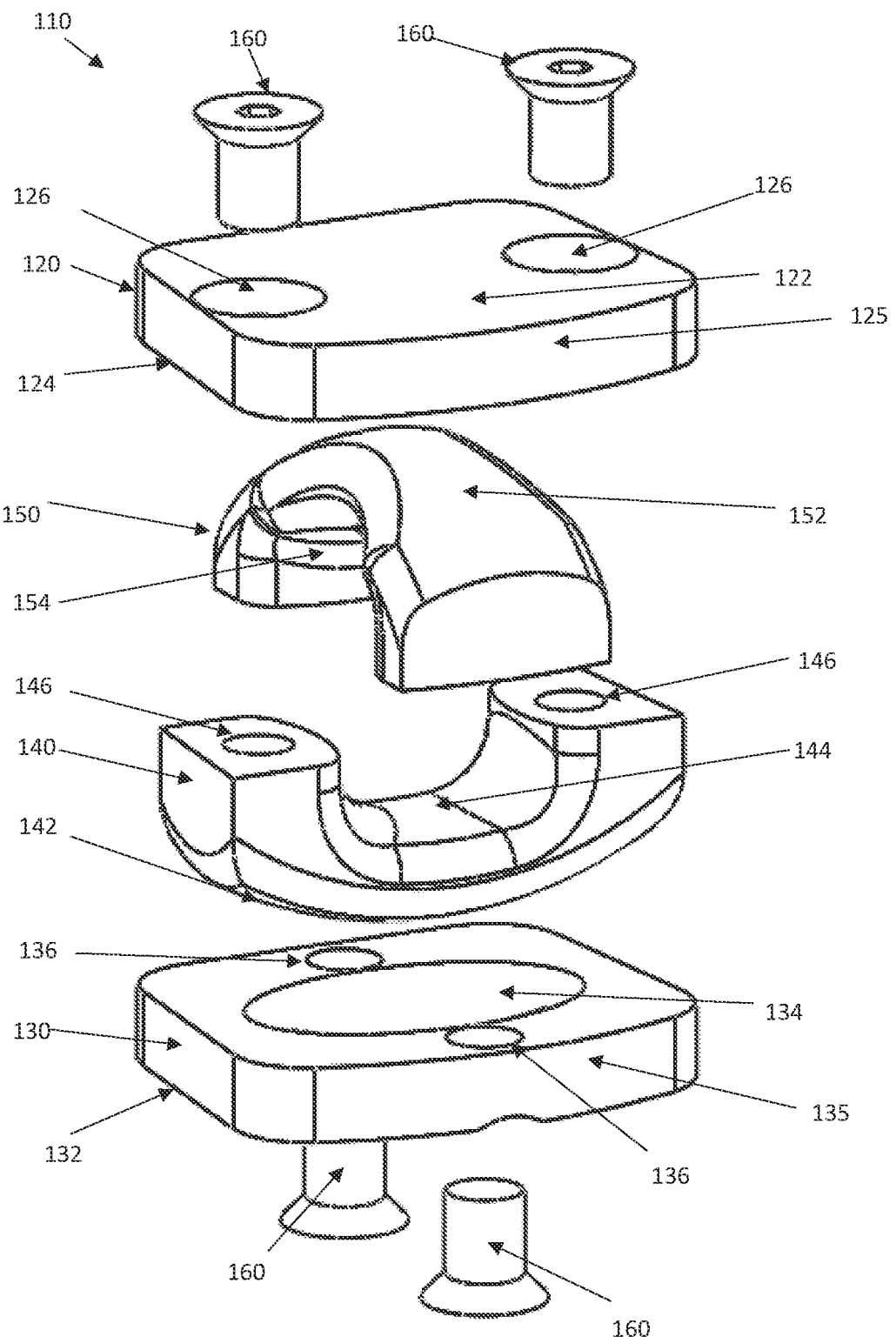
FIG. 11 is an exploded view of a prosthetic spinal disc in accordance with a second embodiment of the present invention.

FIG. 11 is an exploded view of a prosthetic spinal disc in accordance with a second embodiment of the present invention. In the depicted example, the first u-shaped element 140 and the second u-shaped element 150 are fastened to the first base 125 and the second base 135, respectively, by fasteners 160. In some embodiments, the first base 125 and the second base 135 may each include one or more fastening holes 136 for receiving fasteners 160 configured to secure the u-shaped elements to the bases. In some embodiments, the u-shaped elements 140 and 150 include one or more holes 146 configured to receive the fasteners 160 and fasten the u-shaped elements 140 and 150 to the first base 125 and the second base 135, respectively. In the illustrated example, the fasteners 160 extend through the fastening holes 126 and 136 and into holes 146 disposed on the first u-shaped element 140 and the second u-shaped element 150, respectively. In some embodiments the holes 146 are threaded, corresponding to the threads of the fasteners 160. In accordance with various embodiments, the first u-shaped element 140 is configured to articulate against and interlock with the second u-shaped element 150.

In an example illustrative of the design and operation of various embodiment implementations, to assemble the prosthetic spinal disc 110, the two u-shaped elements 140 and 150 are configured to correspond with one another. In various embodiments, the two u-shaped elements 140 and 150 may be fastened to the first base 125 and the second base 135, respectively, with fasteners 160. In some embodiments, the interior articulating surface 144 of the first u-shaped element 140 may be configured to connect with the interior articulating surface 154 of the second u-shaped element 150. In an illustrative example, the interior articulating surface 144 of the first u-shaped element 140 may be configured to articulate against the interior articulating surface 154 of the second u-shaped element 150. In various embodiments, the first u-shaped element 140 and the second u-shaped element 150 may interlock with one another, to prevent the two components from separating. In any embodiment, the width of the u-shaped elements 140 and 150 may define the bounds of articulation of the first and second endplate components 120 and 130.

In another example illustrative of the design and operation of various embodiment implementations, the interlocked u-shaped elements 140 and 150 may be configured to prevent over extension of the vertebral joint once the prosthetic spinal disc 110 is implanted. Moreover, the opposing orientation of the u-shaped element 140 and the u-shaped element 150 may prevent over-rotation of each of the first and second endplate components 120 and 130, respectively. In an illustrative example, the second u-shaped element 150 and the first u-shaped element 140 may be configured to rest against and limit the movement one another as the prosthetic spinal disc 110 moves or rotates with the joint.

In another example illustrative of the design and operation of various embodiment implementations, the magnetic portion of the first endplate component 120 and the magnetic portion of the second endplate component 130 may be configured to repel each other to prevent excess movement in the longitudinal or vertical axis once the prosthetic implant 110 is implanted. Accordingly, the opposing forces of the magnetic portions of the first and second endplate components 120 and 130 may be configured to absorb shock, similar to the natural shock absorption of a natural disc. The magnetic portions may also be configured to prevent excess compression, approximation and distraction, in turn, limiting or preventing the creation of wear debris between the first base 125 and the second base 135.

Figure 12:
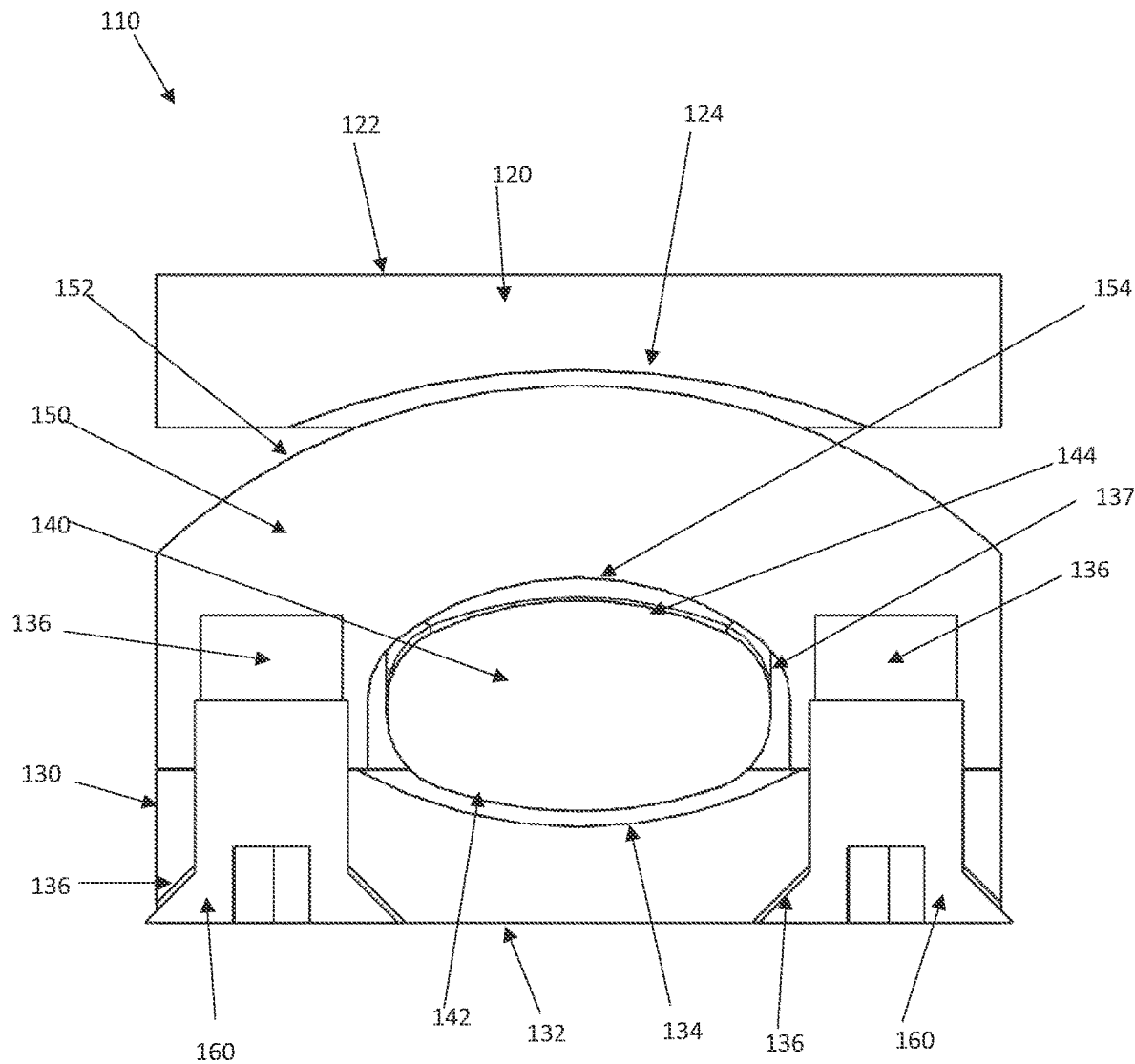
FIG. 12 is a lateral cross-sectional view of a prosthetic spinal disc in accordance with a second embodiment of the present invention.

FIG. 12 is a lateral cross sectional view of a prosthetic spinal disc in accordance with a second embodiment of the present invention. In the depicted embodiment, an aperture 127 is disposed between the first u-shaped element 140 and the interior surface of the first base 125. In the depicted example, the aperture 127 is configured to receive the second u-shaped element 150.

Figure 13:
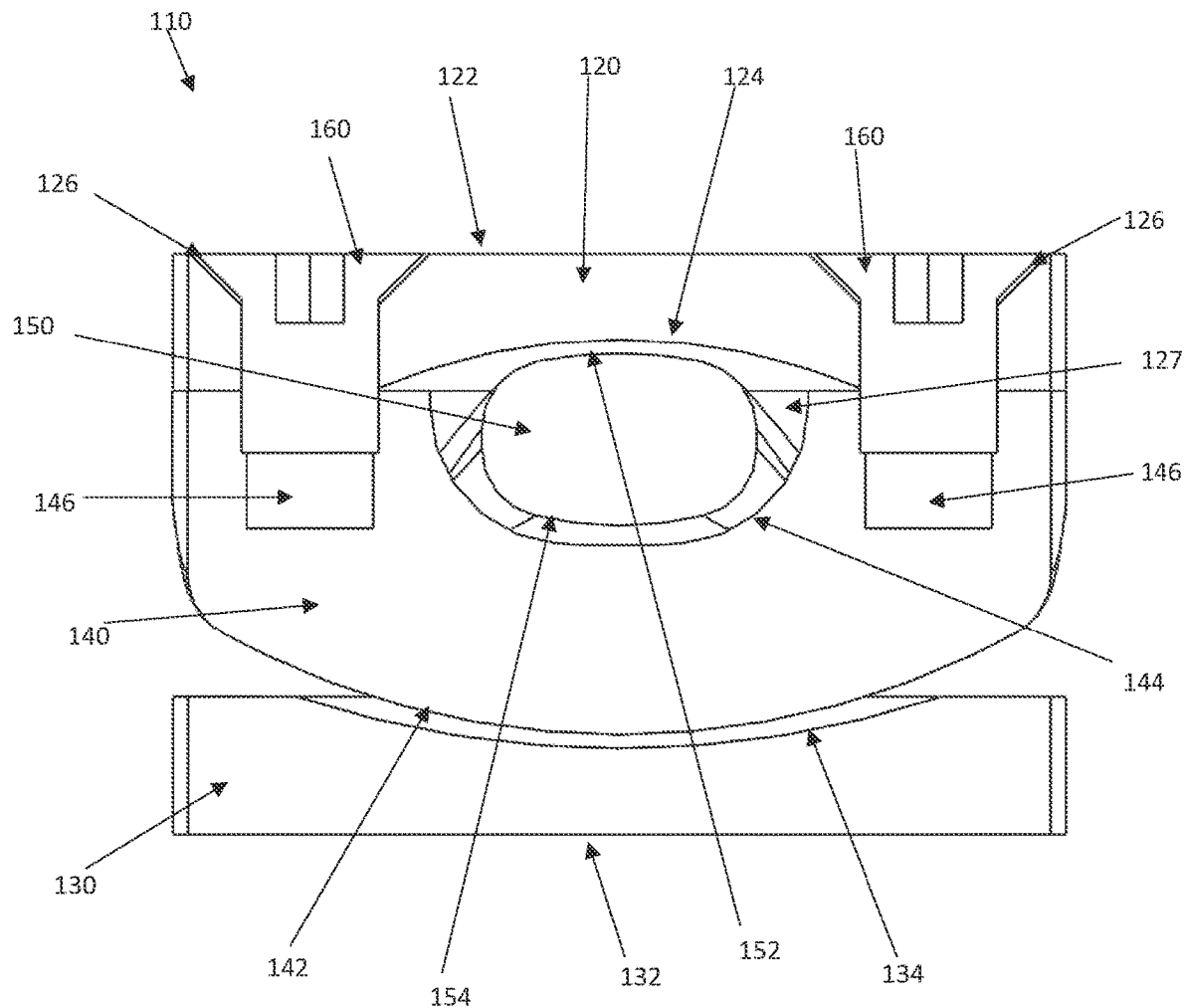
FIG. 13 is an anterior cross-sectional view of a prosthetic spinal disc in accordance with a second embodiment of the present invention.

FIG. 13 is an anterior cross sectional view of a prosthetic spinal disc in accordance with a second embodiment of the present invention. In the depicted embodiment, an aperture 137 is disposed between the second u-shaped element 150 and the interior surface of the second base 135. In the depicted example, the aperture 137 is configured to receive the first u-shaped element 140.

Third Exemplary Embodiment

Figure 14:
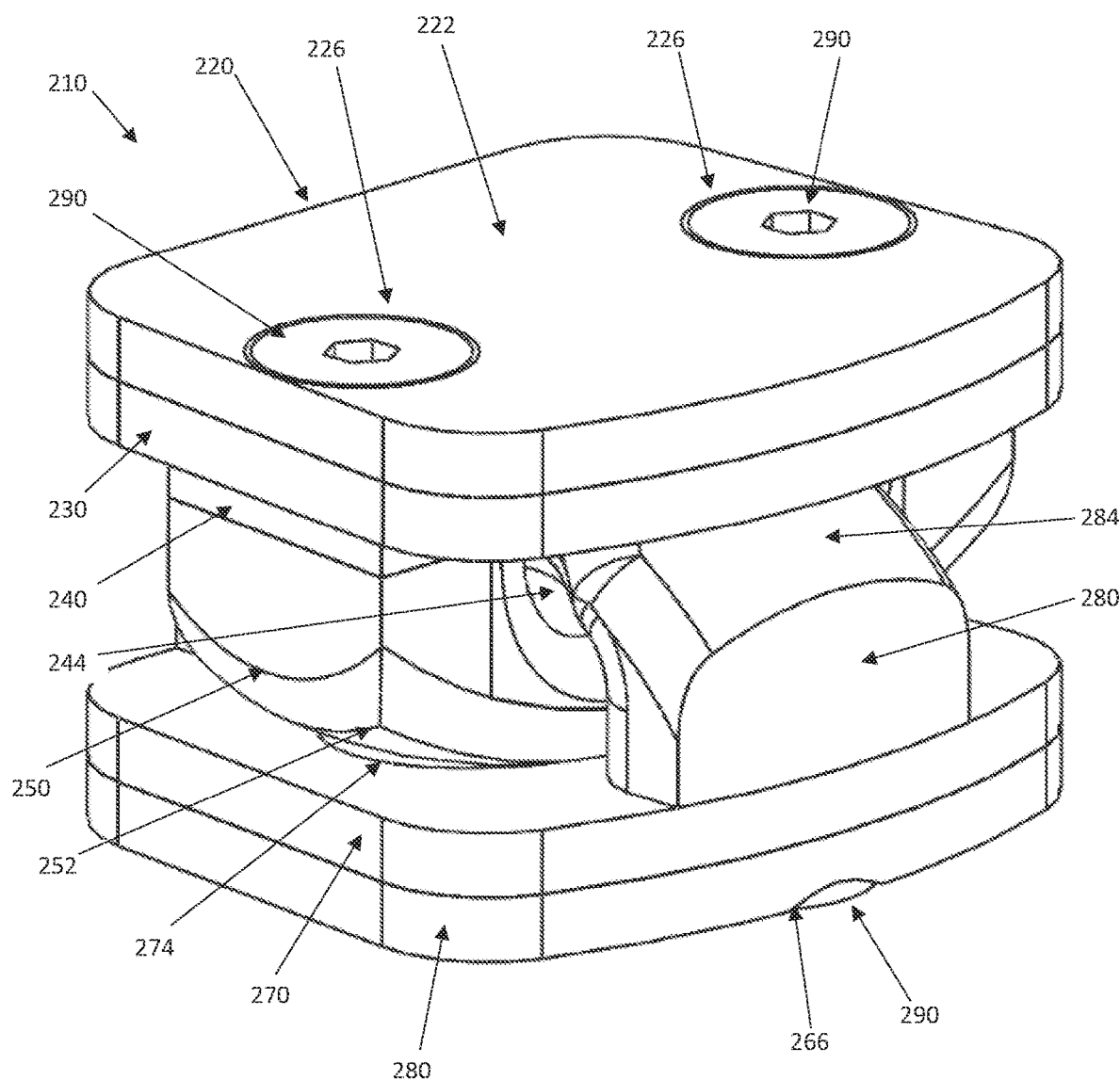
FIG. 14 is a perspective view of a prosthetic spinal disc in accordance with a third embodiment of the present invention.

FIG. 14 is a perspective view of a prosthetic spinal disc in accordance with a third embodiment of the present invention. In the depicted example, the prosthetic spinal disc 210 is comprised of a first base 225 and a second base 235. In the illustrated embodiment, the first base 225 is comprised of an interior endplate component 230 and an exterior endplate component 220. In the depicted example, the exterior endplate component 220 is configured to couple with the interior endplate component 230. Similarly, in the illustrated embodiment, the second base 235 is comprised of an interior endplate component 270 and an exterior endplate component 260. In the depicted example, the exterior endplate component 260 is configured to couple with the interior endplate component 270. In some examples, the first and second bases 225 and 235 may each comprise a magnetic portion. In some embodiments, the interior endplate components 230 and 270 may be magnets. In some embodiments, the interior endplate components 230 and 270 may comprise magnetic portions. In some embodiments, at least one of the exterior endplate component 220, the interior endplate component 230, the exterior endplate component 260, or the interior endplate component 270 are formed of ultra-high-molecular-weight polyethylene (UHMWPE) material. One of ordinary skill in the art would appreciate that there are numerous suitable and advantageous materials for creating endplate components 220, 230, 260, and 270, including other elastomeric materials, metal or ceramic, depending on the specific intended use application of the particular prosthetic spinal discs, and embodiments of the present invention are contemplated for use with any such materials.

Figure 15:
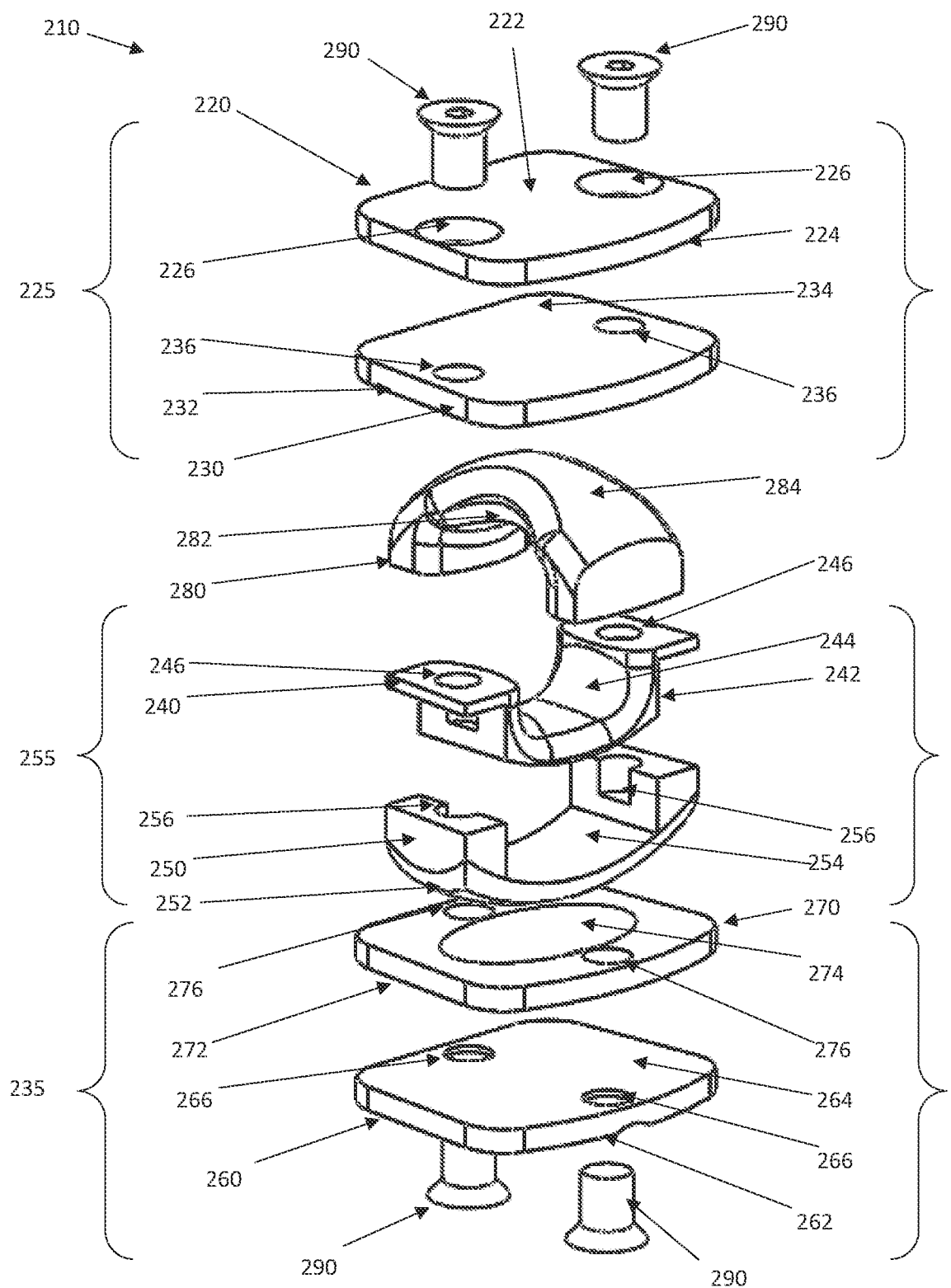
FIG. 15 is an exploded view of a prosthetic spinal disc in accordance with a third embodiment of the present invention.

FIG. 15 is an exploded view of a prosthetic spinal disc in accordance with a third embodiment of the present invention. In the illustrated embodiment, a first u-shaped element 255 is comprised of an inner u-shaped member 240 and an outer u-shaped member 250. In the depicted embodiment, the outer u-shaped member 250 is configured to receive the inner u-shaped member 240. In some embodiments, at least one of the inner u-shaped member 240 and the outer u-shaped member 250 are partially or substantially formed of UHMWPE material. In the depicted embodiment, the first u-shaped element 255 is configured to connect with the first base 225. In a preferred embodiment, the inner u-shaped member 240 connects to the interior endplate component 230 of the first base 225. In the depicted example, fasteners 290 connect the first u-shaped element 255 to the first base 225. In the illustrated embodiment, apertures 226 and 236 in the exterior endplate component 220 and the interior endplate component 230, respectively, are configured to receive fasteners 290 to secure the first u-shaped element 255 to the first base 225. In any embodiment, the fasteners 290 may be screws, pins, or any similar fastening members. In a preferred embodiment, the fasteners 290 connect the exterior endplate component 220 to the interior endplate component 230, the inner u-shaped element 240 and the outer u-shaped element 250. In the depicted embodiment, the inner u-shaped element 240 and the interior endplate component 230 are configured to be sandwiched between the exterior endplate component 220 and the outer u-shaped element 250.

As further shown in FIG. 15, a second base 235 may be comprised of an interior endplate component 270 and an exterior endplate component 260. In the depicted example, the exterior endplate component 260 is configured to couple with the interior endplate component 270. In some embodiments, at least one of the exterior endplate component 260 and the interior endplate component 270 are partially or substantially formed of UHMWPE material. In the depicted embodiment, a second u-shaped element 280 is configured to connect with the second base 235. In the depicted example, fasteners 290 connect the second u-shaped element 280 to the first base 235. In any embodiment, the fasteners 290 may be screws, pins, or any similar fastening members. In the illustrated example, the first u-shaped element 255 is configured to trap the second u-shaped element 280 between itself and the interior endplate component 230. Likewise, in the depicted example, the second u-shaped element 280 is configured to trap the first u-shaped element 255 between itself and the interior endplate component 270. In some examples, the first u-shaped element 255 is configured to articulate between the second u-shaped element 280 and the interior endplate component 270. Similarly, in some scenarios, the second u-shaped element 280 is configured to articulate between the first u-shaped element 255 and the interior endplate component 230. One of ordinary skill in the art would appreciate that there are numerous suitable and advantageous materials for creating the u-shaped elements 255 and 280, including other elastomeric materials, metal or ceramic, depending on the specific intended use application of the particular prosthetic spinal discs, and embodiments of the present invention are contemplated for use with any such materials.

In some examples, the exterior endplate component 220 includes a vertebral mating surface 222 on its exterior face. In some scenarios, the interior face of the exterior endplate component 220 includes an interior endplate component mating surface 224, configured to mate the exterior endplate component 220 to the interior endplate component 230. In some embodiments, the interior endplate component mating surface 224 is a UHMWPE mating surface. In some embodiments, the interior endplate component mating surface 224 may be generally flat, but configured to grip, by means of a roughened surface or adhesive, the interior endplate component 230. The exterior endplate component 220 may include one or more apertures 126 configured to receive fasteners 290. In some examples, the vertebral mating surface 222 may include spikes, teeth, porous areas, and similar texture and surface options which provide for improved mating with vertebral bodies. In some embodiments, the exterior endplate component 220 may be comprised of a metal such as stainless steel or cobalt chrome alloy. One of ordinary skill in the art would appreciate that there are numerous suitable and advantageous arrangements for endplate components 220, 230, 260, and 270 depending on the specific intended use application of the particular prosthetic spinal discs and embodiments of the present invention are contemplated for use with any such prosthetic spinal disc arrangements.

In some scenarios, the interior face of the interior endplate component 230 includes an exterior endplate component mating surface 234, configured to mate the interior endplate component 230 to the exterior endplate component 220. In some examples, opposite of the exterior endplate component mating surface 234 of the interior endplate component 230, is a base articulation surface 232. In some embodiments, the base articulation surface 232 may be flat. In some embodiments, the base articulation surface 232 may be concave. In some examples, the interior endplate component 230 includes one or more apertures 136 configured to receive fasteners 290.

Figure 16:
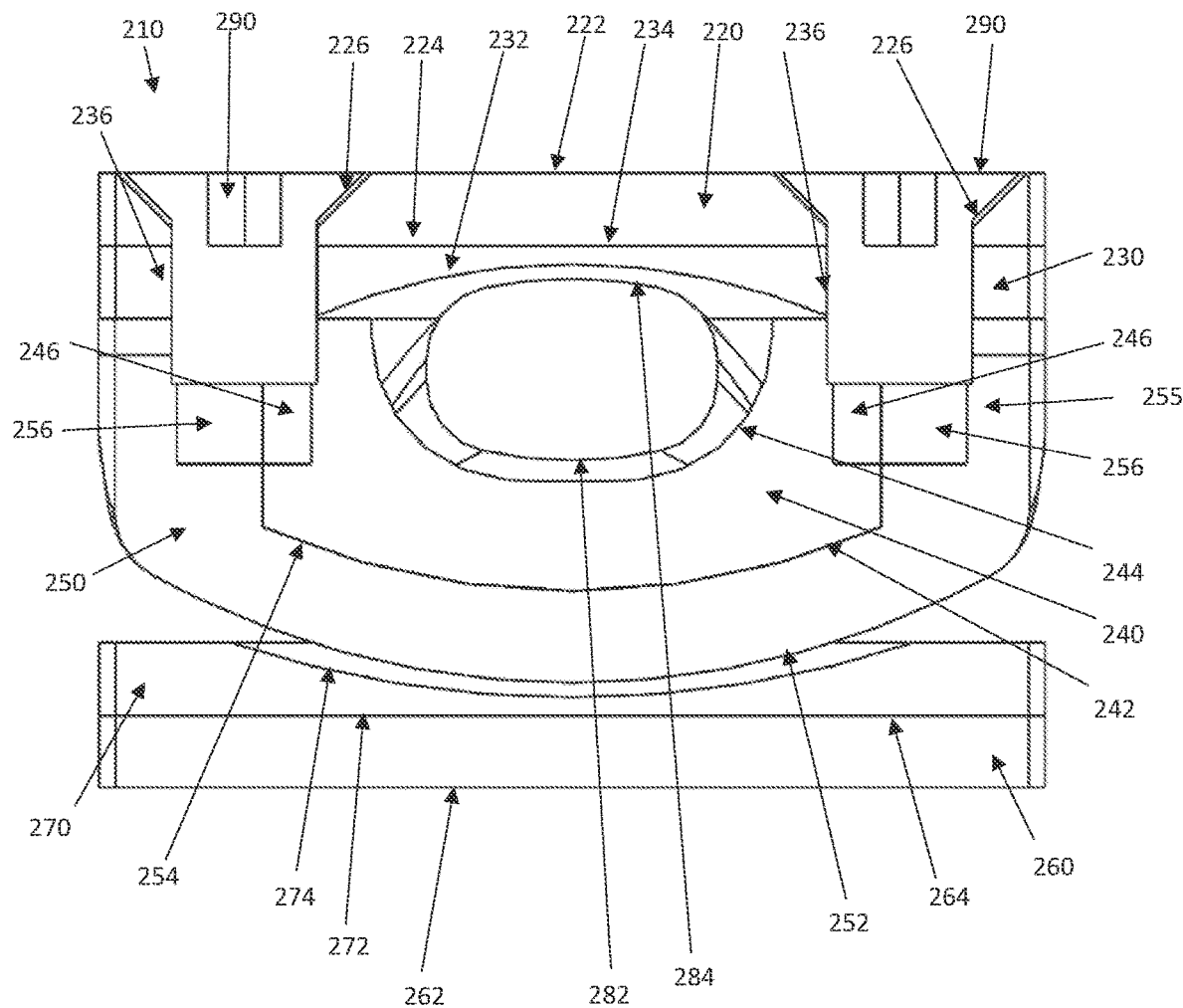
FIG. 16 is an anterior cross-sectional view of a prosthetic spinal disc in accordance with a third embodiment of the present invention.

FIG. 16 is an anterior cross sectional view of a prosthetic spinal disc in accordance with a third embodiment of the present invention. In the illustrated embodiment, the first u-shaped element 255 is configured to connect and couple with the first base 225. In the depicted example, the interior endplate component 230 is disposed between the first u-shaped element 255 and the exterior endplate component 220. In the depicted example, apertures 226 and 236 of the exterior endplate component 220 and the interior endplate component 230, respectively, are configured to receive fasteners 290 to secure the first u-shaped element 255 to the first base 225. In the depicted example, the first u-shaped element 255 is configured to rest and articulate against the base articulation surface 274 of the interior endplate component 270. In some embodiments, the first u-shaped element 255 comprises an exterior articulating surface 252 and an interior articulating surface 244. In some embodiments, the exterior articulating surface 252 is generally convex. In some embodiments, the interior articulating surface 244 is generally concave. In some examples, the first u-shaped element 255 extends from one side of the first base 225 to a second side of the base 225.

Figure 17:
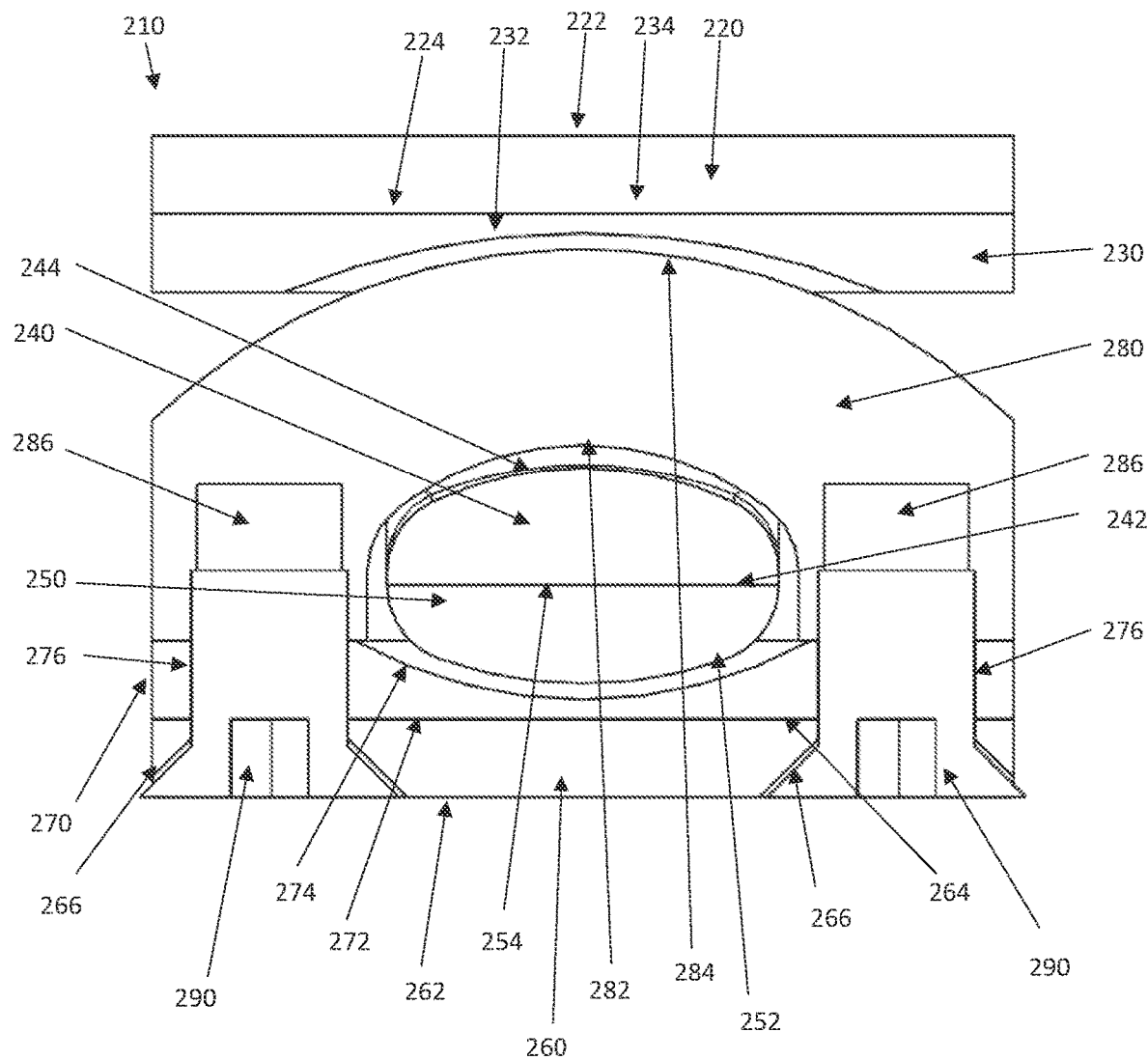
FIG. 17 is a lateral cross-sectional view of a prosthetic spinal disc in accordance with a third embodiment of the present invention.

FIG. 17 is a lateral cross sectional view of a prosthetic spinal disc in accordance with a third embodiment of the present invention. In the illustrated embodiment, the second u-shaped element 280 is configured to connect and couple with the second base 235. In the depicted example, the interior endplate component 270 is disposed in between the exterior endplate component 260 and the second u-shaped element 280. In the depicted example, apertures 266 and 276 of the exterior endplate component 260 and the interior endplate component 270 are configured to receive fasteners 290 to secure the second u-shaped element 280 to the second base 235. In the depicted example, the second u-shaped element 280 is configured to rest and articulate against the base articulation surface 232 of the interior endplate component 230. In some embodiments, the second u-shaped element 280 comprises an exterior articulating surface 284 and an interior articulating surface 282. In some embodiments, the exterior articulating surface 284 is generally convex. In some embodiments, the interior articulating surface 282 is generally concave. In some examples, the second u-shaped element 280 generally extends from one side of the second base 235 to a second side of the base 235. In some embodiments, the first u-shaped element 255 and the second u-shaped element 280 may be comprised of a polyethylene material or a metal such as stainless steel or cobalt chrome alloy. One of ordinary skill in the art would appreciate that there are numerous suitable and advantageous materials for creating the u-shaped elements 255 and 280, depending on the specific intended use application of the particular prosthetic spinal discs and embodiments of the present invention are contemplated for use with any such materials.

In an example illustrative of the design and operation of various embodiment implementations, the prosthetic spinal disk 220 may be assembled with the first u-shaped element 255 mated with the second u-shaped element 280. The two u-shaped elements 255 and 280 are configured to fasten to their corresponding bases 225 and 235, respectively, by fasteners 290. In some examples, the exterior articulating surface 252 of the first u-shaped element 255 is configured to rest and articulate on the base articulation surface 274 of the interior endplate component 270. Similarly, in some scenarios, the base articulation surface 232 of the interior endplate component 230 is configured to rest and articulate on the exterior articulating surface 284 of the second u-shaped element 280.

In some examples, the interior articulating surface 144 of the first u-shaped element 255 is configured to connect with the interior articulating surface 282 of the second u-shaped element 280. In an illustrative example, the interior articulating surface 244 of the first u-shaped element 255 is configured to articulate against the interior articulating surface 282 of the second u-shaped element 280. In various embodiments, the u-shaped element 255 of the first base 225 and the u-shaped element 280 of the second base 235 interlock with one another, preventing the two components from separating.

In another example illustrative of the design and operation of various embodiment implementations, the interlocked u-shaped elements 255 and 280 may be configured to prevent over extension of the vertebral joint once the prosthetic spinal disc 210 is implanted. Moreover, the opposing orientation of the first u-shaped element 255 and the second u-shaped element 280 may prevent over-rotation of each of the first and second bases 225 and 235, respectively. In an illustrative example, the second u-shaped element 280 and the first u-shaped element 255 are configured to rest against and limit the movement of one another as the prosthetic spinal disc 210 articulates, rotates or moves with the joint.

In another example illustrative of the design and operation of various embodiment implementations, the magnetic portion of the first base 225 and the magnetic portion of the second base 235 may be configured to repel each other to prevent excess movement in the longitudinal or vertical axis once the prosthetic implant 210 is implanted. Accordingly, the opposing forces of the magnetic portions of the first and second bases 225 and 235 may be configured to absorb shock, similar to the natural shock absorption of a natural disc. The magnetic portions may also be configured to prevent excess compression, approximation and distraction, in turn, limiting or preventing the creation of wear debris between the first base 225 and the second base 235.

Fourth Exemplary Embodiment

Figure 18:
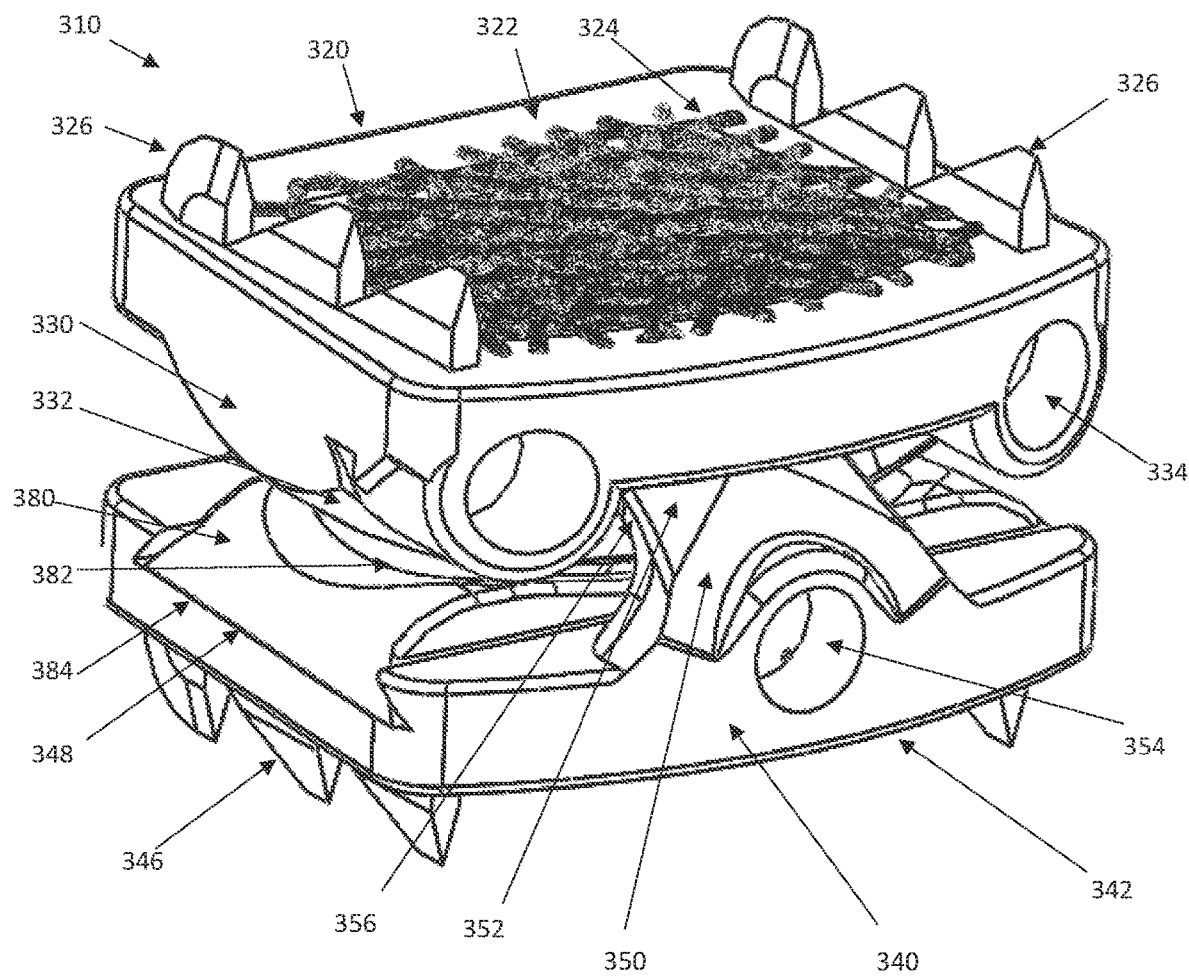
FIG. 18 is a perspective view of a prosthetic spinal disc in accordance with a fourth embodiment of the present invention.

FIG. 18 is a perspective view of a prosthetic spinal disc in accordance with a fourth embodiment of the present invention. In the illustrated embodiment, the prosthetic spinal disc 310 is comprised of a first endplate component 320 and a second endplate component 340. In the illustrated example, the first endplate component 320 and the second endplate component 340 include fastening apertures 334. In any embodiment, one or more fastening apertures 334 may be disposed on either or both of the first and second endplate components 320 and 340. The fastening apertures 334 may be configured to receive and engage with a fastener (not shown) in order to secure the disc 310 to bone. In the depicted embodiment, the first endplate component 320 and the second endplate component 340 each include a vertebral mating surface 322 and 342, respectively, on an exterior portion of the component. In the illustrated embodiment, the vertebral mating surface 322 includes a porous bone ingrowth surface 324 to promote bone mating and growth. In the depicted embodiment, the vertebral mating surface 322 of the first endplate component 320 and the vertebral mating surface 342 of the second endplate component 340 each include a plurality of keels 326. In any embodiment, the vertebral mating surfaces 322 and 342 may include one or more keels 326. The keels 326 may be configured to cut into vertebral bodies. In some embodiments, the keels 326 may be configured as teeth or any other feature to cut into the vertebral bodies to prevent migration. One of ordinary skill in the art would appreciate that there are numerous suitable and advantageous arrangements for the keels depending on the specific intended use application of the particular prosthetic spinal implant and embodiments of the present invention are contemplated for use with any such prosthetic spinal implant arrangements.

Figure 19:
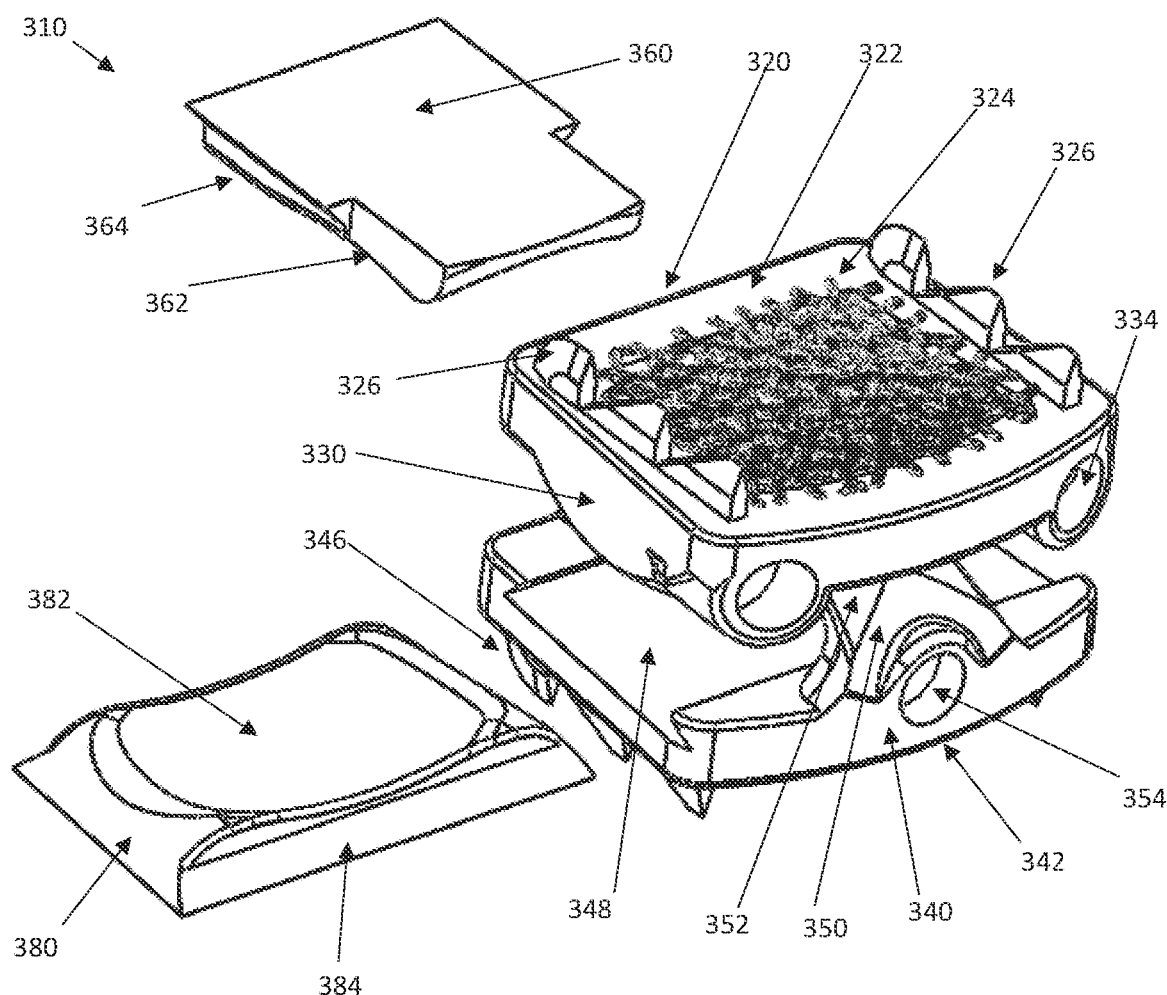
FIG. 19 is a partially unassembled view of a prosthetic spinal disc in accordance with a fourth embodiment of the present invention.

FIG. 19 is a partially unassembled view of a prosthetic spinal disc in accordance with a fourth embodiment of the present invention. In the illustrated example, the prosthetic spinal disc 310 is comprised of a first endplate component 320 and a second endplate component 340. In the depicted example, the first endplate component 320 comprises a first base 325, a first platform component 360, and a first u-shaped element 330. In some embodiments, the first endplate component 320 may further comprise a magnetic portion. In some embodiments, the first platform component 360 may comprise the magnetic portion. In some embodiments, the first platform component 360 may be a magnet. Similarly, in the illustrated example, the second endplate component 340 comprises a second base 335, a second platform component 380, and a second u-shaped element 350. In some embodiments, the second endplate component 340 may further comprise a magnetic portion. In some embodiments, the second platform component 380 may comprise the magnetic portion. In some embodiments, the second platform component 380 may be a magnet. In some embodiments, the u-shaped elements 330 and 350 are flexible. In some embodiments, the u-shaped elements 330 and 350 are configured to selectively deform. In some examples, the first platform component 360 is configured to slidably engage with and lock into the first endplate component 320. Similarly, in some embodiments, the second platform component 380 is configured to slidably engage with and lock into the second endplate component 340. In the depicted example, the first platform component 360 includes a base articulation surface 362 configured to articulate against the exterior articulating surface 352 of the second endplate component 340. In the illustrated example, the base articulation surface 362 is generally convex. In some examples, the base articulation surface 362 may be concave. In some embodiments, any of the bases 325 and 335, the platform components 360 and 380, and the u-shaped elements 330 and 350 may be partially or substantially formed of a UHMWPE material. One of ordinary skill in the art would appreciate that there are numerous suitable and advantageous materials for creating the bases 325 and 335, the platform components 360 and 380, and the u-shaped elements 330 and 350, including other elastomeric materials, metal or ceramic, depending on the specific intended use application of the particular prosthetic spinal discs, and embodiments of the present invention are contemplated for use with any such materials.

Figure 20:
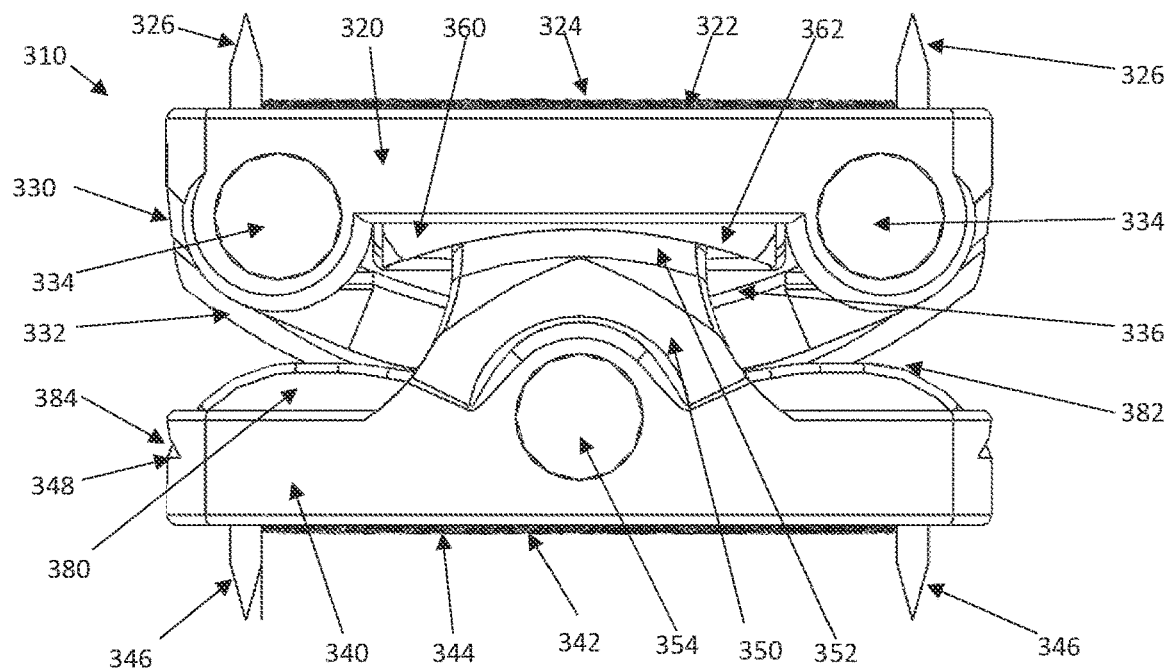
FIG. 20 is an anterior view of a prosthetic spinal disc in accordance with a fourth embodiment of the present invention.
Figure 21:
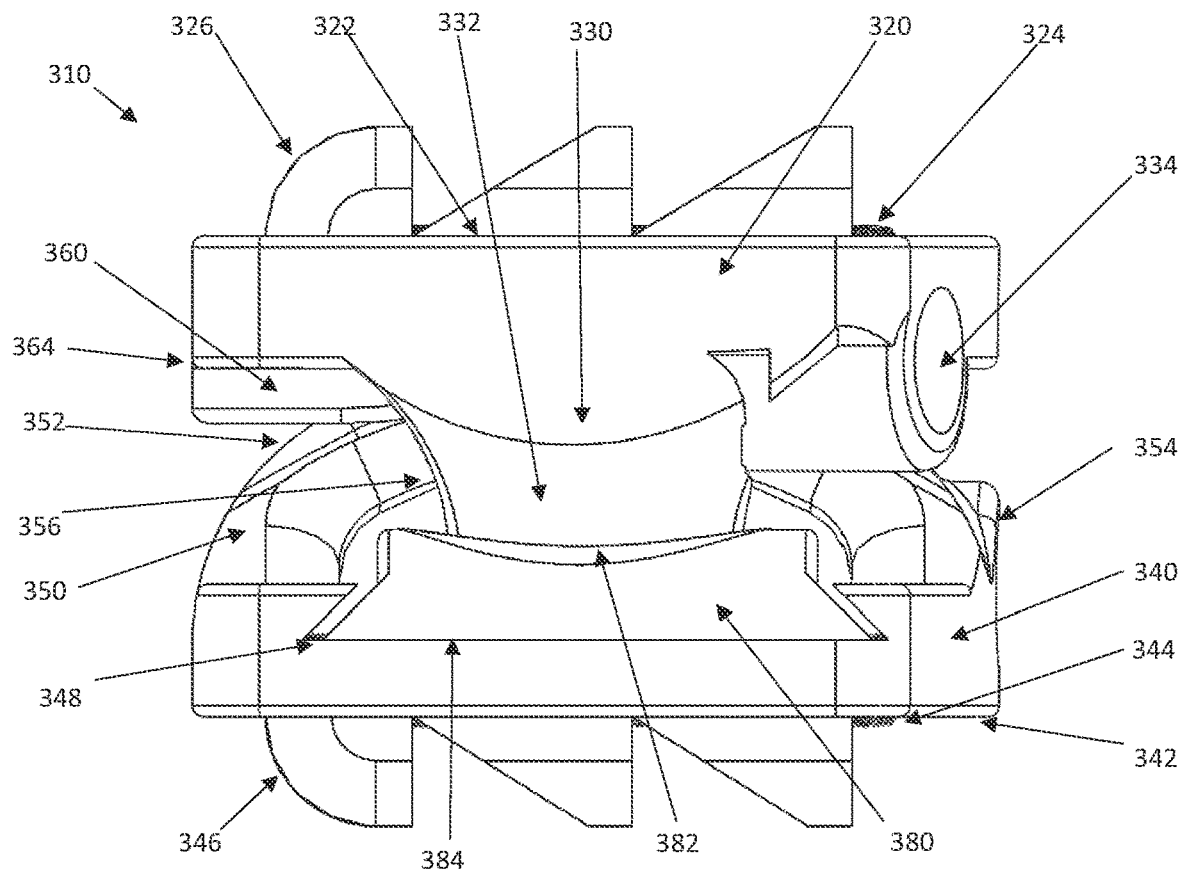
FIG. 21 is a lateral view of a prosthetic spinal disc in accordance with a fourth embodiment of the present invention.

FIGS. 20 and 21 depict a prosthetic spinal disc in accordance with a fourth embodiment of the present invention. In the illustrated embodiment, the vertebral mating surface 342 includes a porous bone ingrowth surface 344. In some embodiments, the first platform component 360 is configured to slide between the first endplate component 320 and the exterior articulating surface 352 of the second endplate component 340. In some embodiments, an interior portion of the first base 325 may be dove-tailed to accept the first platform component 360. In the illustrated embodiment, extending from the first base 325 is the u-shaped element 330 comprising an exterior articulating surface 332 and an interior articulating surface 336. In the depicted example, the exterior articulating surface 332 is generally convex and the interior articulating surface 336 is generally concave. In the illustrated example, the u-shaped element 330 of the first endplate component 320 extends from one side of the first base 325 to a second side of the base 325. In the depicted embodiment, the second platform mating surface 348 is disposed on the interior face of the second endplate component 340. In some embodiments, the second platform mating surface 348 may be dove-tailed to accept the second platform component 380. In the illustrated embodiment, extending from the second base 335 is the u-shaped element 350 comprising an exterior articulating surface 352 and an interior articulating surface 356. In the depicted example, the exterior articulating surface 352 is generally convex and the interior articulating surface 356 is generally concave. In the illustrated example, the u-shaped element 350 of the second endplate component 340 extends from a first side of the second base 335 to a second side of the base 335.

Figure 22:
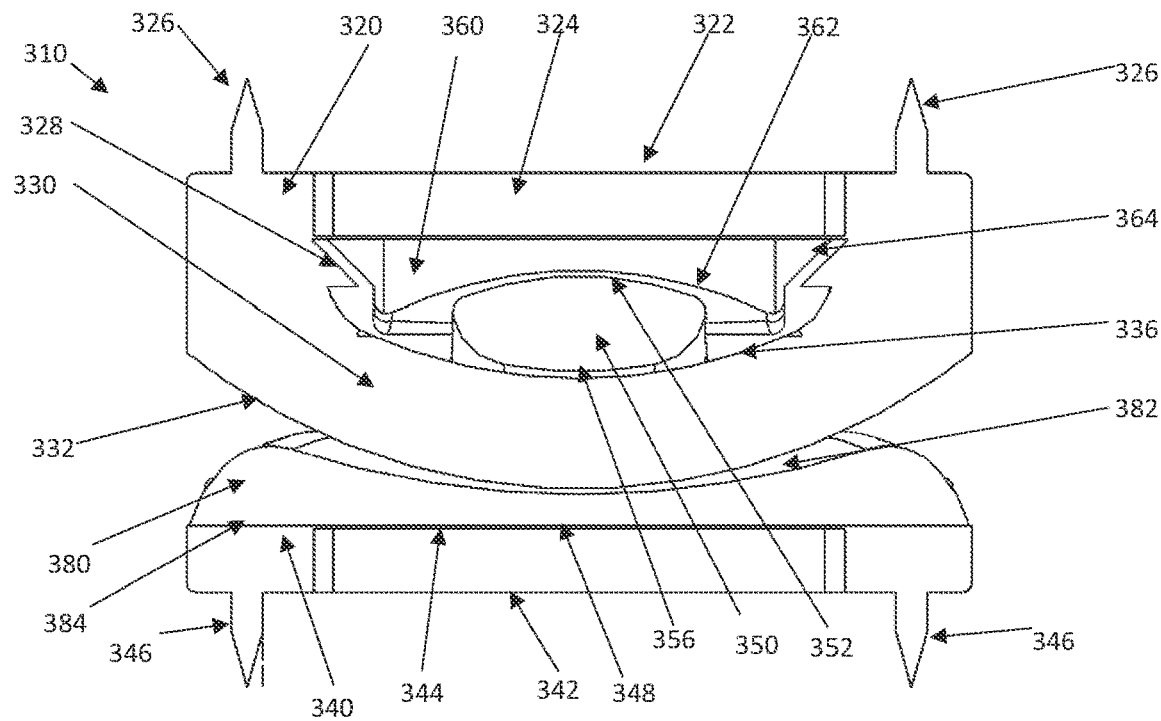
FIG. 22 is an anterior cross-sectional view of a prosthetic spinal disc in accordance with a fourth embodiment of the present invention.
Figure 23:
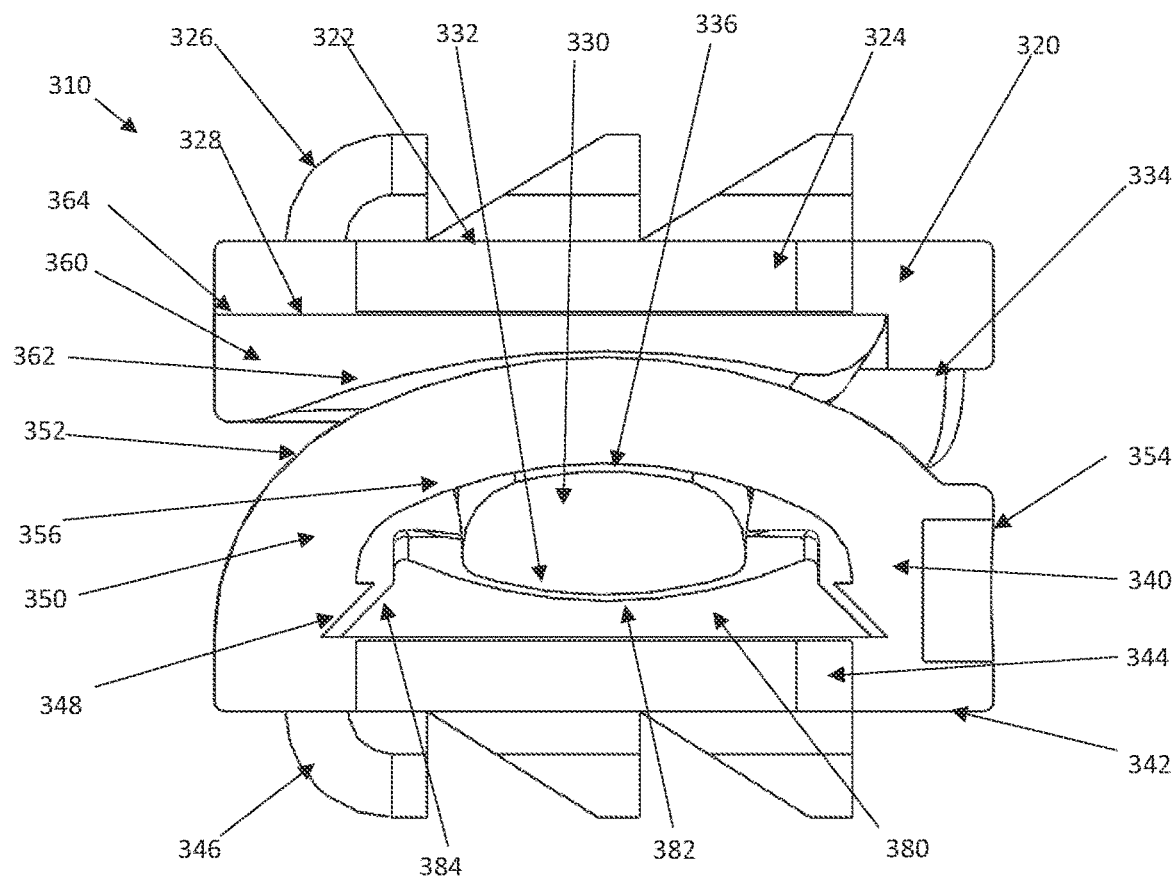
FIG. 23 is a lateral cross-sectional view of a prosthetic spinal disc in accordance with a fourth embodiment of the present invention.

FIGS. 22 and 23 depict a prosthetic spinal disc in accordance with a fourth embodiment of the present invention. In the depicted example, the second endplate component 340 includes one or more fastening apertures 354. In the illustrated example, the first platform component 360 includes an endplate mating surface 364 configured with a locking mechanism to lock with the platform component mating surface 328 of the first endplate component 320. Similarly, in the illustrated embodiment, the second platform component 380 includes an endplate mating surface 348 configured with a locking mechanism to lock with the platform mating surface 348 of the second endplate component 380. In some embodiments, the locking mechanism is a dovetail locking mechanism.

As shown in FIG. 22, the second platform component 380 may be configured to slide between the second endplate component 340 and the exterior articulating surface 332 of the first endplate component 320. In the illustrated embodiment, the second platform component 380 includes a base articulation surface 382 configured to articulate against the exterior articulating surface 332 of the first endplate component 320. In the depicted embodiment, the base articulation surface 382 is generally convex. In some examples, the base articulation surface 382 may be concave.

In an example illustrative of the design and operation of various embodiment implementations, the prosthetic spinal disc 310 and/or any components thereof may be 3D printed. For example, the first endplate component 320 may be printed concurrently with the second endplate component 340. Therefore, the u-shaped element 330 of the first endplate component 320 and the u-shaped element 350 of the second endplate component 340 may be integrally formed with their respective bases, and printed simultaneously, so that they are interlocking with one another. In some scenarios, once the first endplate component 320 and second endplate component 340 are printed, the first platform component 360 and second platform component 380 may slide and lock into place in the first and second bases 325 and 335, respectively. In some examples, the exterior articulating surface 332 of the first endplate component 320 may be configured to rest and articulate on the base articulation surface 382 of the second platform component 380. Similarly, the base articulation surface 362 of the first platform component 360 is configured to rest and articulate on the exterior articulating surface 352 of the second endplate component 340.

In another example illustrative of the design and operation of various embodiment implementations, the interlocked u-shaped elements 330 and 350 may prevent over extension of the vertebral joint once the prosthetic spinal disc 310 is implanted. Moreover, the opposing orientation of the u-shaped element 330 and the u-shaped element 350 may prevent over-rotation of each of the first and second endplate components 320 and 340, respectively. In an illustrative example, the second u-shaped element 350 and the first u-shaped element 330 may be configured to rest against and limit the movement of one another as the prosthetic spinal disc 310 rotates with the joint.

In another example illustrative of the design and operation of various embodiment implementations, the magnetic portion of the first endplate component 320, for example, the magnetic portion of the first platform component 360 and the magnetic portion of the second endplate component 340, for example, the magnetic portion of the second platform component 380 may be configured to repel each other to prevent excess movement in the longitudinal or vertical axis once the prosthetic implant 310 is implanted. Accordingly, the opposing forces of the magnetic portions of the first and second endplate components 320 and 340 may be configured to absorb shock, similar to the natural shock absorption of a natural disc. The magnetic portions may also be configured to prevent excess compression, approximation and distraction, in turn, limiting or preventing the creation of wear debris between the first base 325 and the second base 335.

Fifth Exemplary Embodiment

Figure 24:
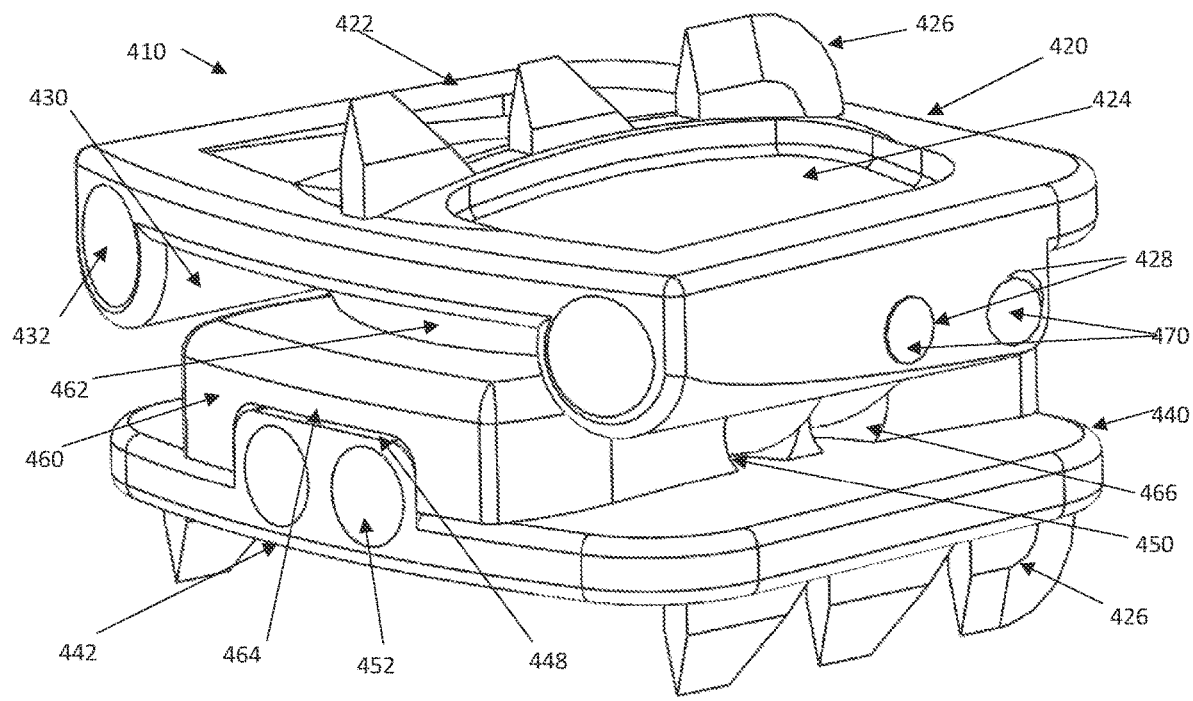
FIG. 24 is a perspective view of a prosthetic spinal disc in accordance with a fifth embodiment of the present invention.

FIG. 24 is a perspective view of a prosthetic spinal disc in accordance with a fifth embodiment of the present invention. In the illustrated embodiment, the prosthetic spinal disc 410 is comprised of a first endplate component 420, a second endplate component 440, an articulating element 460, and one or more connector rods 470. In some embodiments, the first endplate component 420 includes one or more elongate extensions 430. In the illustrated example, the first endplate component 420 includes two elongate extensions 430. In the depicted example, each elongate extension 430 includes an inserter aperture 432. In some embodiments, the inserter apertures 432 are configured to engage with an inserter (not shown). In some scenarios an inserter (not shown) is used to connect to and hold the disc 410 while the disc 410 is inserted into a patient body during a given procedure. In some embodiments, the elongate extensions 430 include rod apertures 428. In the illustrated embodiment, the rod apertures 428 are configured to correspond to the shape of the connector rods 470 and fasten the connector rods 470 to the first endplate component. In some examples, the elongate extensions 430 may be crimped or deformed to hold or secure the connector rods 470 in place. In some embodiments, the connector rods 470 may be connected and secured to the elongate extensions 430 using a fastener such as a screw, pin or similar fastening member. In the depicted embodiment, the first endplate component 420 and the second endplate component 440 each include a vertebral mating surface 422 and 442, respectively, on an exterior portion of the component. In the illustrated embodiment, the vertebral mating surface 422 includes a porous bone ingrowth surface 424 to promote bone mating and growth. In the depicted embodiment, the vertebral mating surface 422 of the first endplate component 420 and the vertebral mating surface 442 of the second endplate component 440 each include a plurality of keels 426. In any embodiment, the vertebral mating surfaces 422 and 442 may include one or more keels 426 configured to cut into vertebral bodies. In some embodiments, the keels 426 may be configured as teeth or any other feature to cut into the vertebral bodies to prevent migration.

Figure 25:
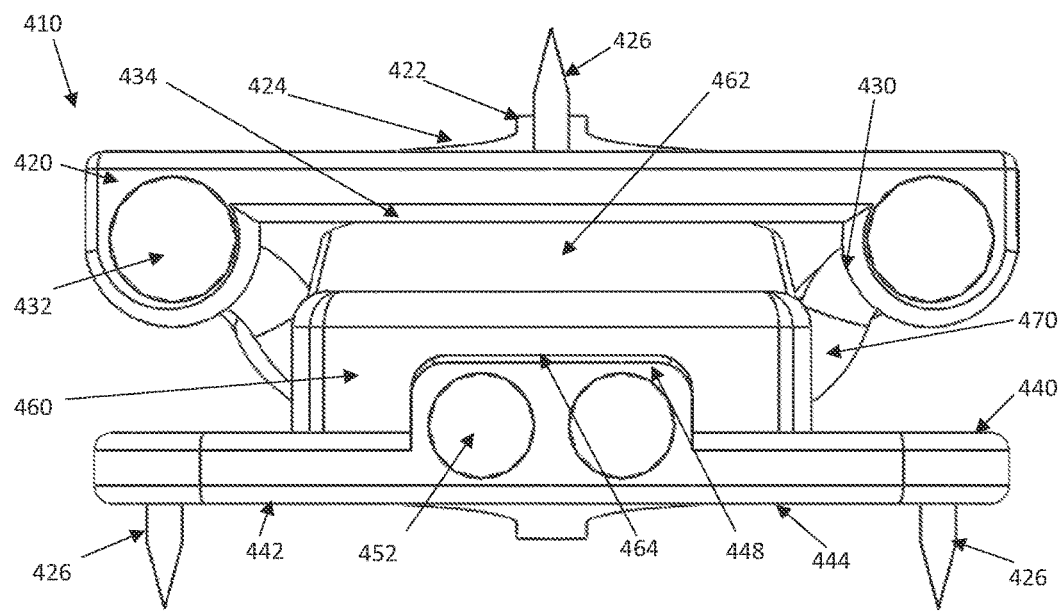
FIG. 25 is an anterior view of a prosthetic spinal disc in accordance with a fifth embodiment of the present invention.
Figure 26:
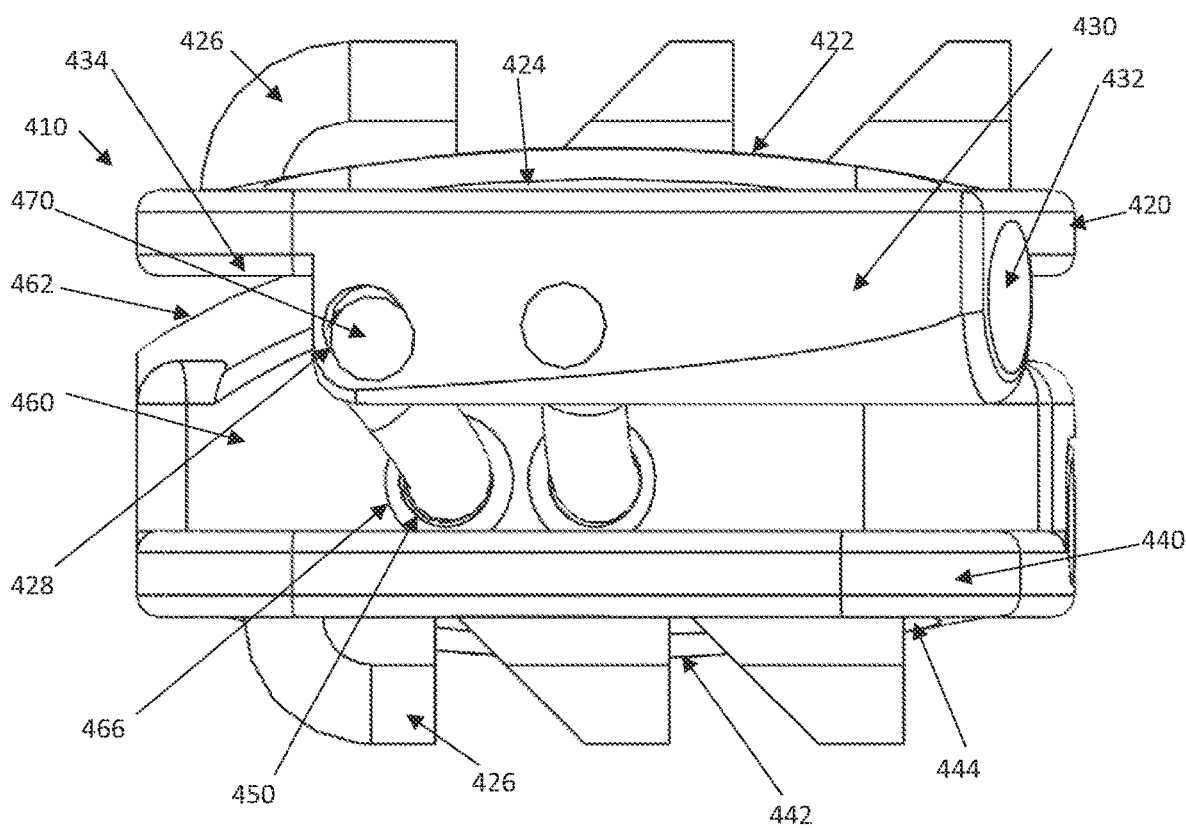
FIG. 26 is a lateral view of a prosthetic spinal disc in accordance with a fifth embodiment of the present invention.

FIGS. 25 and 26 depict a prosthetic spinal disc in accordance with a fifth embodiment of the present invention. In some embodiments, the vertebral mating surface 442 of the second endplate component 440 includes a porous bone ingrowth surface 444 to promote bone mating and growth. In some embodiments, the first endplate component 420 includes an articulating surface 434, a magnetic portion, and one or more connector rods 470. In some embodiments, the articulating surface 434 of the first endplate component 420 is generally concave. In the illustrated embodiment, two connector rods 470 extend from the first endplate component 420. In some embodiments, the connector rods 470 are flexible. In the depicted example, the two connector rods 470 of the first endplate component 420 each extend from one side of the first endplate component 420 to a second side of the first endplate component 420. In the illustrated embodiment, extending from the inner surface of the second endplate component 440 is a protruding platform 448 configured to connect to an articulating element 460. In some embodiments, the second endplate component 440 includes a magnetic portion configured to repel the magnet portion of the first endplate component 420. In some embodiments, the articulating element 460 has a substantially rectangular frame and is configured to protrude from the second endplate component 440 and includes an exterior articulating surface 462. In some embodiments, the exterior articulating surface 462 of the articulating element 460 is generally convex. In some embodiments, the articulating element 460 may have a generally round, oval, triangular or any other geometrically shaped frame. In some embodiments, the articulating element 460 includes one or more outer apertures 466 configured to receive one or more connector rods 470. In some embodiments, the protruding platform 448 includes one or more inner apertures 450 configured to receive one or more connector rods 470. In some embodiments, the articulating element 460 is partially or substantially formed of UHMWPE material. In the depicted example, the articulating element 460 includes a convex surface configured as an exterior articulating surface 462. In some embodiments, the exterior articulating surface 462 is substantially flat. In the depicted embodiment, the connector rods 470 extend across the articulating element 460, through outer apertures 466 and inner apertures 450. In some embodiments, the connector rods 470 are inserted through outer apertures 466 and inner apertures 450 to fasten the articulating element 460 to the second endplate component 440. In some embodiments, the apertures 450 and 466 are configured to allow one or more connector rods 470 to slightly move within the articulating element 460 while securing the articulating element 460 to the second endplate component 440. In some embodiments, the apertures 450 and 466, either alone or in combination, are configured to prevent the connector rods 470 from moving anterior-posterior or cephalad-caudal in relation to the second endplate component 440. One of ordinary skill in the art would appreciate that there are numerous suitable and advantageous arrangements for the articulating element depending on the specific intended use application of the particular prosthetic spinal disc and embodiments of the present invention are contemplated for use with any such prosthetic spinal disc arrangements.

In some embodiments, the connector rods 470 are comprised of a flexible material such as NiTiNol wire, UHMWPE fibers, or similar material. In some embodiments, the connector rods 470 are held securely at each end within the rod apertures 428 in the first endplate component 420. In some embodiments, a middle portion of each connector rod 470 is retained within inner apertures 450 disposed on the articulating element 460. In some embodiments, the connector rods 470 are configured to connect the first endplate component 420 to the second endplate component 440, while also holding the articulating element 460 substantially in place. In some embodiments, the flexibility of the connector rods 470 permits the first endplate component 420 to move and rotate with respect to the second endplate component 440, while substantially preventing over-rotation.

Figure 27:
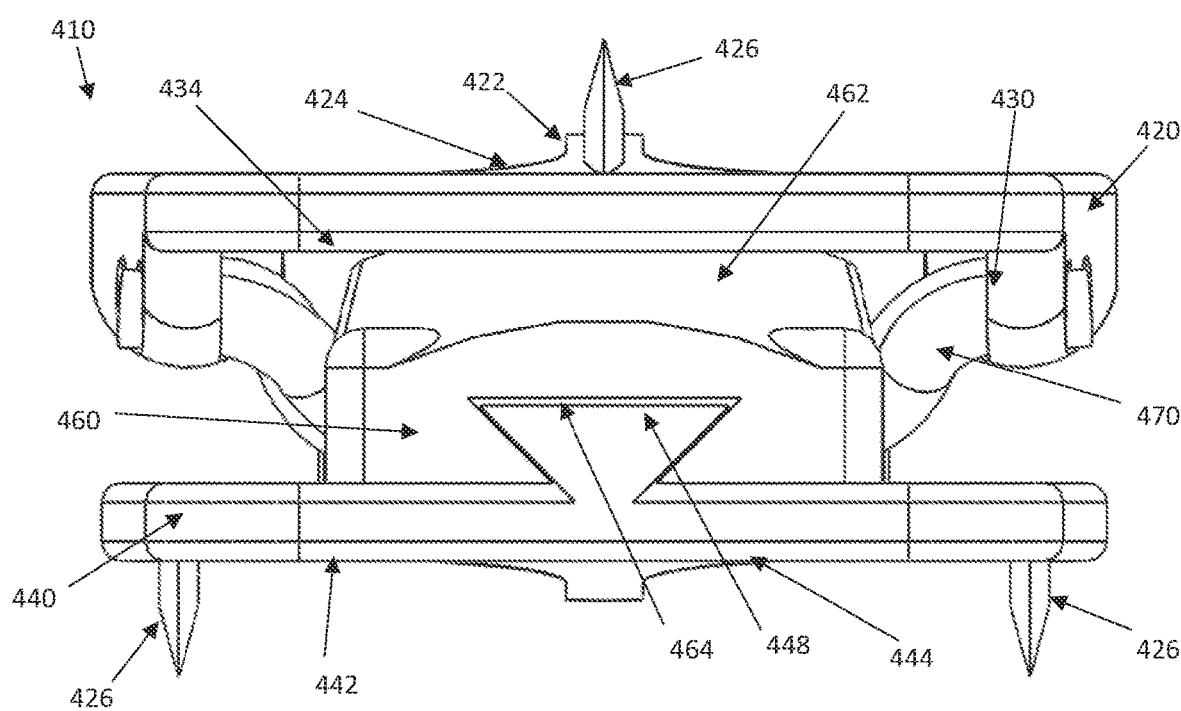
FIG. 27 is a cross sectional view of a prosthetic spinal disc in accordance with a fifth embodiment of the present invention.

FIG. 27 depicts a cross-sectional view of a prosthetic spinal disc in accordance with a fifth embodiment of the present invention. In some embodiments, the articulating element 460 includes an endplate mating means configured to fasten the articulating element 460 to the second endplate component 440. In the illustrated embodiment, the endplate mating means is an indentation 464 in the articulating element 460 configured to mate with the protruding platform 448 on the second endplate component 440. In the depicted embodiments, the indentation 464 and the protruding platform 448 are configured in corresponding dovetail orientations which are adapted to secure the the articulating element 460 to the second endplate component 440. In the depicted example, the articulating element 460 is disposed between the first endplate component 420 and the second endplate component 440. In some embodiments, the articulating element 460 includes an articulation surface 462 configured to rest or articulate against the articulating surface 434 of the first endplate component 420.

In an example illustrative of the design and operation of various embodiment implementations, the exterior articulating surface 462 of the articulating element 460 is configured to rest and articulate on the articulation surface 434 of the first endplate component 420. In some examples, the connector rods 470 extend across the articulating element 460, through outer apertures 466 and inner apertures 450, to fasten the articulating element 460 to the second endplate component 440 while permitting the one or more connector rods 470 to slightly move within the articulating element 460 to enable the articulating element 460 to articulate against the articulation surface 434 of the first endplate component 420. In various embodiments, articulating element 460 and the one or more connector rods 470 substantially fasten to the articulating element to prevent the two components from separating.

In another example illustrative of the design and operation of various embodiment implementations, the magnetic portion of the first endplate component 420 and the magnetic portion of the second endplate component 440 may be configured to repel each other to prevent excess movement in the longitudinal or vertical axis once the prosthetic implant 410 is implanted. Accordingly, the opposing forces of the magnetic portions of the first and second endplate components 420 and 440 may be configured to absorb shock, similar to the natural shock absorption of a natural disc. The magnetic portions may also be configured to prevent excess compression, approximation and distraction, in turn, limiting or preventing the creation of wear debris between the first endplate component 420 and the second endplate component 440.

Sixth Exemplary Embodiment

FIG. 28 depicts a perspective view of a prosthetic spinal disc in accordance with a sixth embodiment of the present invention. In the illustrated embodiment, the prosthetic spinal disc 510 is comprised of a first endplate component 520, a second endplate component 540, an articulating element 560, and one or more connector rods 570. In some embodiments, the first endplate component 520 includes one or more elongate extensions 530. In the illustrated example, the first endplate component 520 includes two elongate extensions 530. In the depicted example, each elongate extension 530 includes an inserter aperture 532. In some embodiments, the inserter apertures 532 are configured to engage with an inserter (not shown). In some scenarios an inserter (not shown) is used to insert the disc 510 into a patient body during a given procedure. In some embodiments, the elongate extensions 530 include rod apertures 528. In the illustrated embodiment, the rod apertures 528 are configured to correspond to the shape of the connector rods 570 and fasten the connector rods 570 to the first endplate component 520. In the depicted embodiment, the first endplate component 520 and the second endplate component 540 each include a vertebral mating surface 522 and 542, respectively, on an exterior portion of the component. In the illustrated embodiment, the vertebral mating surface 522 includes a porous bone ingrowth surface 524 to promote bone mating and growth. In the depicted embodiment, the vertebral mating surface 522 of the first endplate component 520 and the vertebral mating surface 542 of the second endplate component 540 each include a plurality of keels 526. In any embodiment, the vertebral mating surfaces 522 and 542 may include one or more keels 526 configured to cut into vertebral bodies. In some embodiments, the keels 526 may be configured as teeth or any other feature to cut into the vertebral bodies to prevent migration.

Figure 31:
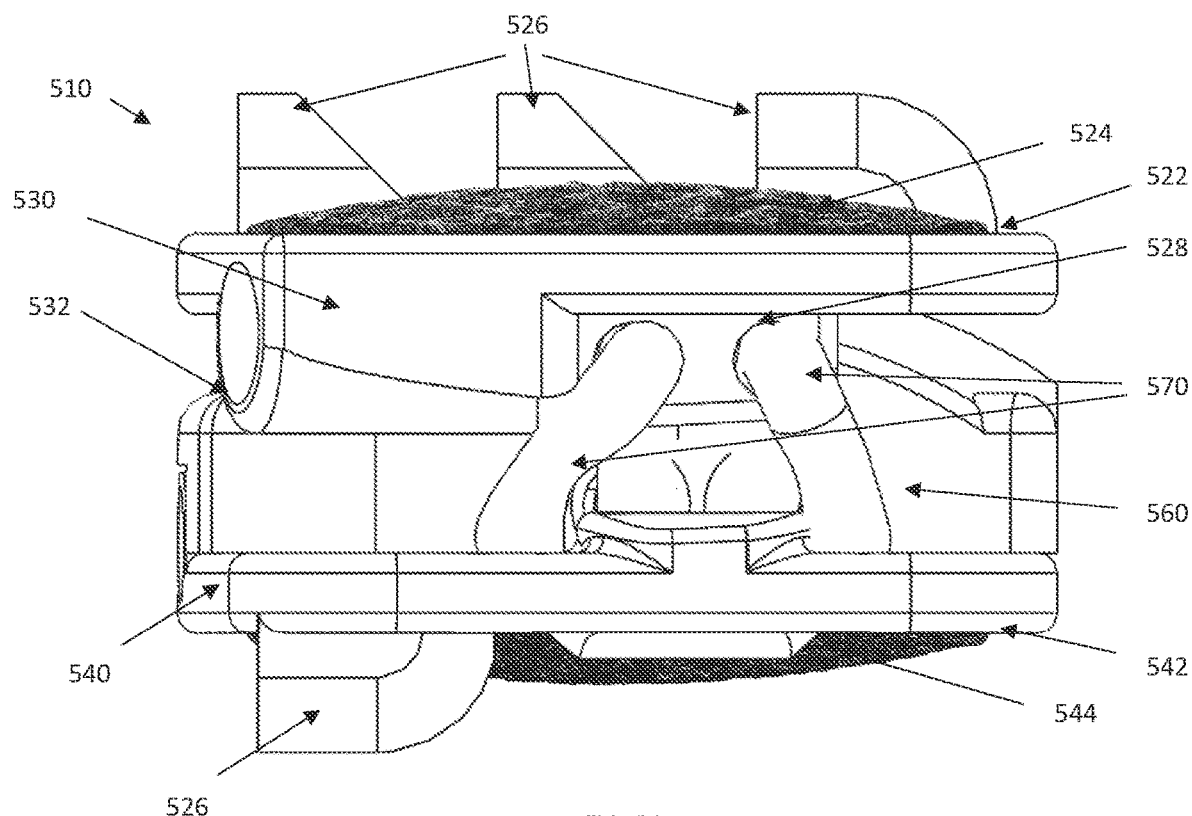
FIG. 31 is a lateral view of a prosthetic spinal disc in accordance with a sixth embodiment of the present invention.

FIGS. 29 and 31 depict a prosthetic spinal disc in accordance with a sixth embodiment of the present invention. In some embodiments, the vertebral mating surface 542 of the second endplate component 540 includes a porous bone ingrowth surface 544 to promote bone mating and growth. In some embodiments, the interior portion of the first endplate component 520 includes an articulating surface 534 and one or more connector rods 570. In some embodiments, the articulating surface 534 of the first endplate component 520 is generally concave. In the illustrated embodiment, two connector rods 570 connect the first endplate component 520 to the second endplate component 540. In some embodiments, the connector rods 570 are flexible. In the depicted example, the connector rods 570 each extend through the articulating element 560 from a first side of the spinal disc 510 to a second side of the spinal disc 510. In the illustrated embodiment, extending from the general central inner surface of the second endplate component 540 is a protruding platform 548 configured to connect to the articulating element 560 having an exterior articulating surface 562 and one or more outer apertures 566 configured to receive one or more connector rods 570. In some embodiments, the protruding platform 548 includes one or more inner apertures 550 configured to receive one or more connector rods 570. In some embodiments, the connector rods 570 connect the articulating element 560 to the protruding platform 548. In some embodiments, the connector rods 570 are inserted through outer apertures 566 and inner apertures 550 to fasten the articulating element 560 to the second endplate component 540. In some embodiments, the connector rods 570 are configured to pass through rod apertures 554, rod apertures 528, outer apertures 566, and inner apertures 550 to generally connect the first endplate 520 to the second endplate 540, as well as to connect both endplates 520 and 540 to the articulating element 560. In some embodiments, the articulating element 560 is partially or substantially formed of UHMWPE material. In the depicted example, the exterior articulating surface 562 of the articulating element 560 is substantially convex. In some embodiments, the exterior articulating surface 562 is substantially flat. In some embodiments, the apertures 550 and 566 are configured to allow one or more connector rods 570 to slightly move within the articulating element 560 while securing the articulating element 560 to the second endplate component 540. In some embodiments, the apertures 550 and 566, either alone or in combination, are configured to prevent the connector rods 570 from moving anterior-posterior or cephalad-caudal in relation to the second endplate component 540.

In some embodiments, the connector rods 570 are comprised of a flexible material such as NiTiNol wire, UHMWPE fibers, or similar material. In some embodiments, the connector rods 570 are held securely at each end within the rod apertures 528 in the first endplate component 520. In some embodiments, a middle portion of each connector rod 570 is retained within inner apertures 550 disposed on the articulating element 560. In some embodiments, the connector rods 570 are configured to connect the first endplate component 520 to the second endplate component 540, while also holding the articulating element 560 substantially in place. As shown in FIG. 28, in some embodiments, the second endplate component 540 includes one or more rod apertures 554. In some embodiments, the rod apertures 554 are configured to receive the connector rods 570 and to fasten the connectors rods 570 to the second endplate component 540. In some embodiments, the flexibility of the connector rods 570 permits the first endplate component 520 to move and rotate with respect to the second endplate component 540, while substantially preventing over-rotation.

Figure 30:
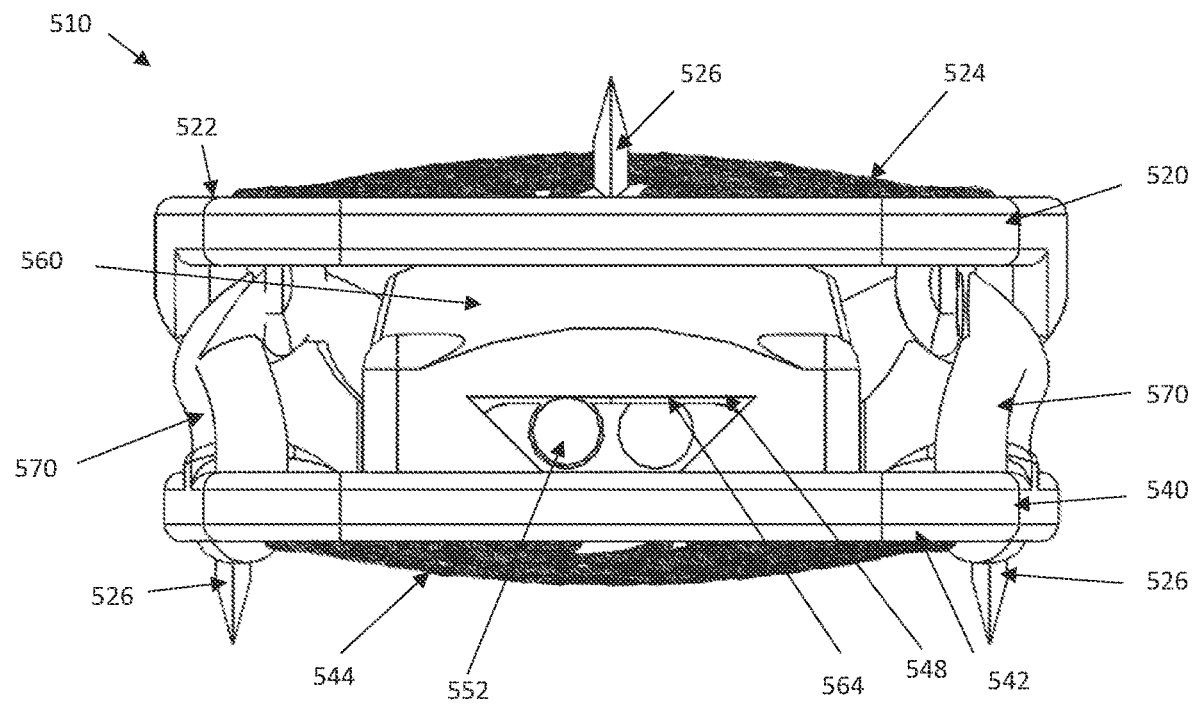
FIG. 30 is a cross sectional view of a prosthetic spinal disc in accordance with a sixth embodiment of the present invention.

FIG. 30 is a cross sectional view of a prosthetic spinal disc in accordance with a sixth embodiment of the present invention. In some embodiments, the articulating element 560 includes an endplate mating means configured to fasten the articulating element 560 to the second endplate component 540. In the illustrated embodiment, the endplate mating means is an indentation 564 in the articulating element 560 configured to mate with the protruding platform 548 on the second endplate component 540. In the depicted embodiments, the indentation 564 and the protruding platform 548 are configured in corresponding dovetail orientations which are adapted to secure the articulating element 560 to the second endplate component 540. In some embodiments, the second endplate component 540 is integrally formed with the articulating element 560. In the depicted example, the articulating element 560 has a generally rectangular frame and is disposed between the first endplate component 520 and the second endplate component 540. In some embodiments, the articulating element 560 includes an articulation surface 562 configured to rest or articulate against the articulating surface 534 of the first endplate component 520.

Figure 32:
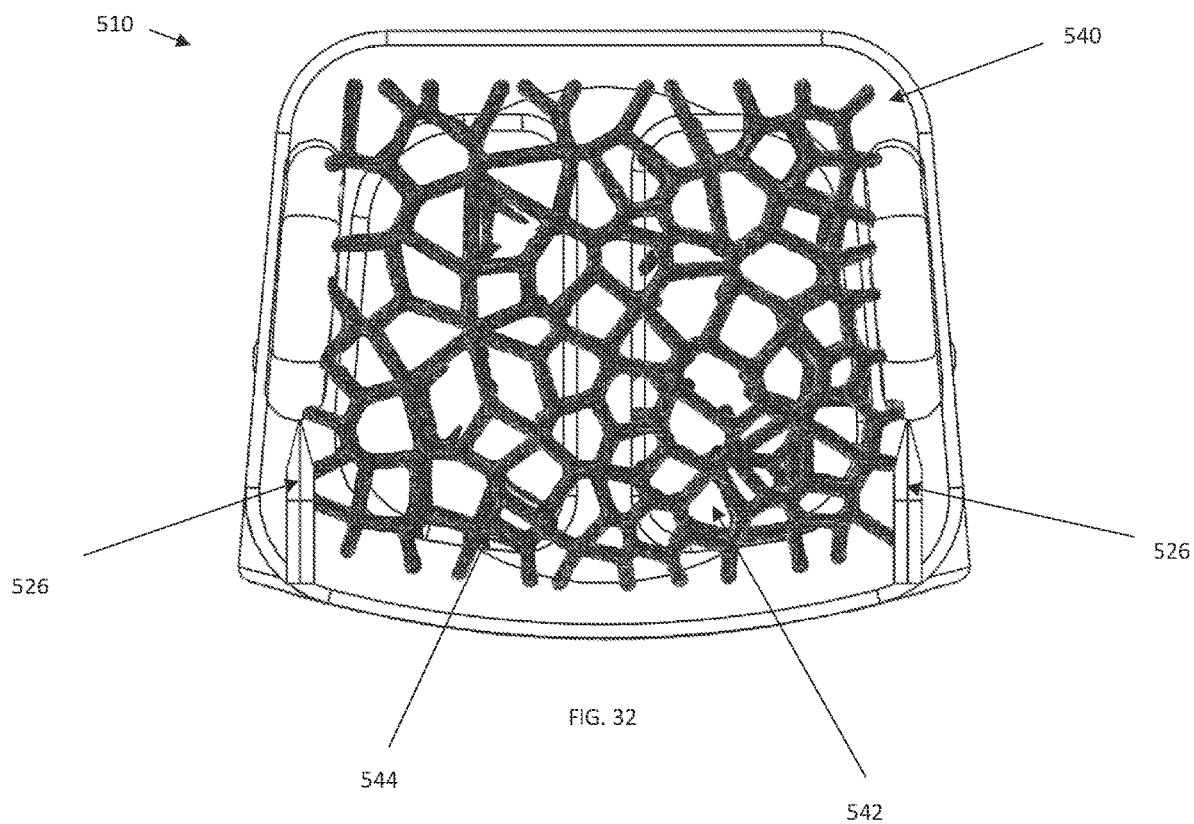
FIG. 32 is a bottom view of a prosthetic spinal disc in accordance with a sixth embodiment of the present invention.
Figure 33:
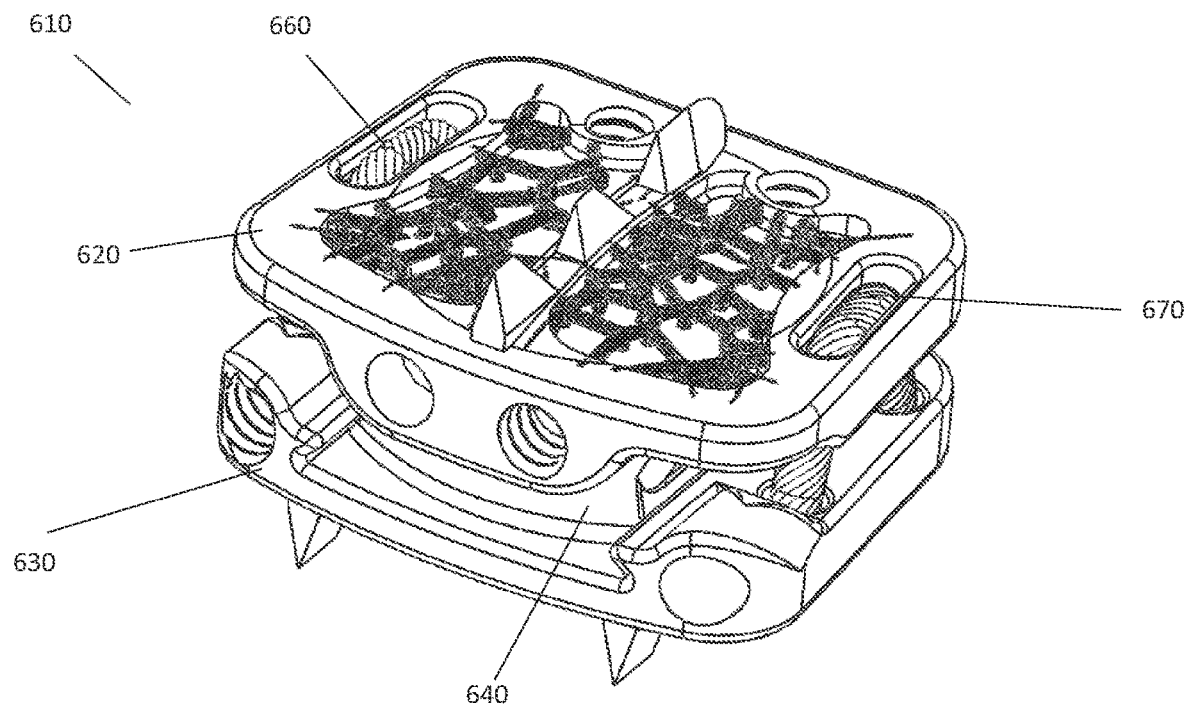
FIG. 33 is a perspective view of a prosthetic spinal disc in accordance with a seventh embodiment of the present invention.
Figure 34:
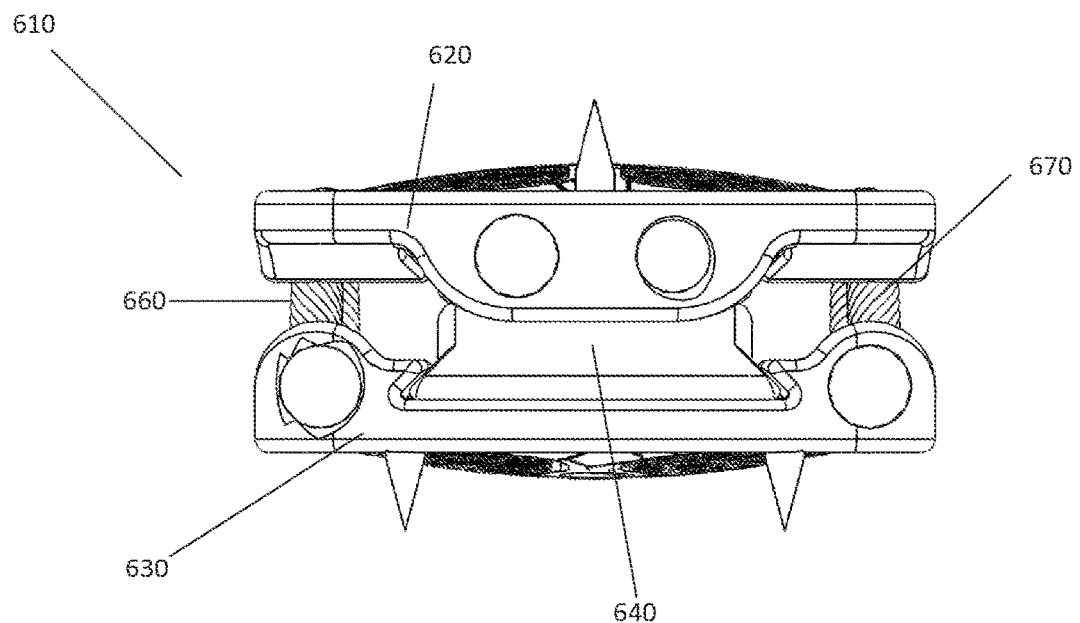
FIG. 34 is an anterior view of a prosthetic spinal disc in accordance with a seventh embodiment of the present invention.
Figure 35:
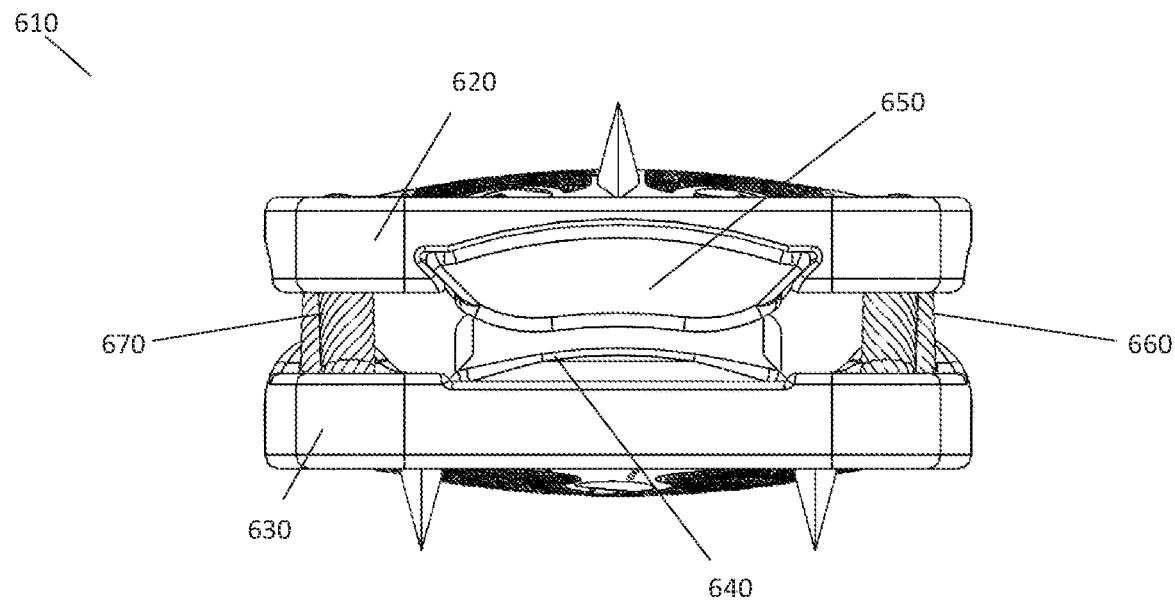
FIG. 35 is a posterior view of a prosthetic spinal disc in accordance with a seventh embodiment of the present invention.
Figure 36:
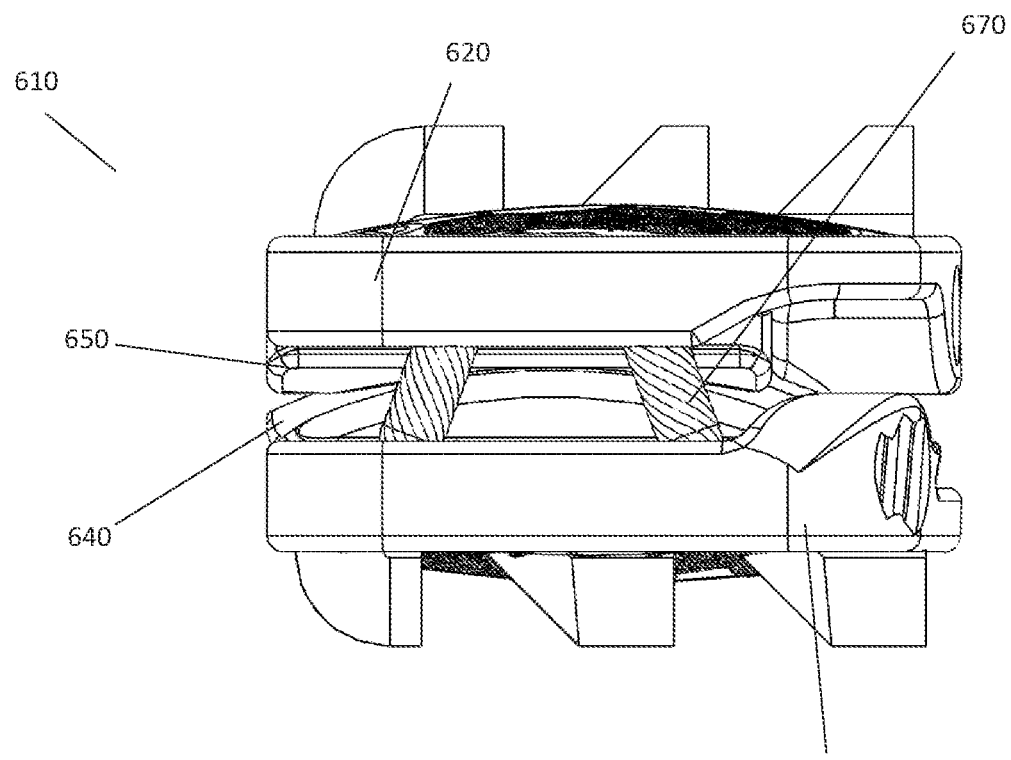
FIG. 36 is a lateral view of a prosthetic spinal disc in accordance with a seventh embodiment of the present invention.
Figure 37:
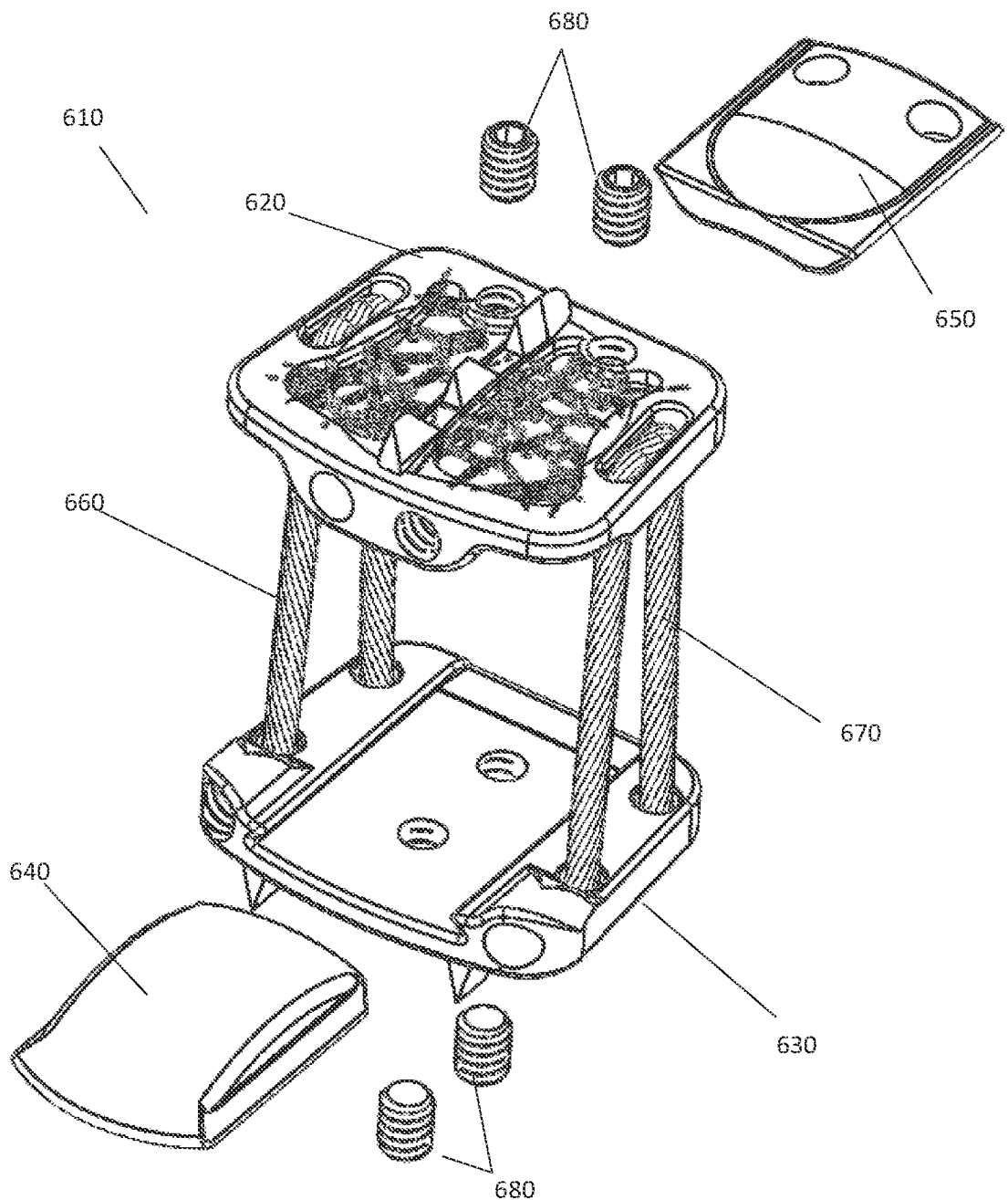
FIG. 37 is an exploded perspective view of a prosthetic spinal disc in accordance with a seventh embodiment of the present invention.

FIG. 32 is a bottom view of a prosthetic spinal disc in accordance with a sixth embodiment of the present invention. In the depicted embodiment, the vertebral mating surface 542 of the second endplate component 540 includes a porous bone ingrowth surface 544 to promote bone mating and growth. In the illustrated embodiment, the second endplate component 540 includes two keels 526.

In an example illustrative of the design and operation of various embodiment implementations, the exterior articulating surface 562 of the articulating element 560 is configured to rest and articulate on the articulation surface 534 of the first endplate component 520. In some examples, the connector rods 570 extend across the articulating element 460 to fasten the articulating element 560 to the second endplate component 540 while permitting the one or more connector rods 570 to slightly move within the articulating element 560 to enable the articulating element 560 to articulate against the articulation surface 534 of the first endplate component 520. In various embodiments, articulating element 560 and the one or more connector rods 570 substantially fasten to the articulating element to prevent the two components from separating.

In another example illustrative of the design and operation of various embodiment implementations, the magnetic portion of the first endplate component 520 and the magnetic portion of the second endplate component 540 may be configured to repel each other to prevent excess movement in the longitudinal or vertical axis once the prosthetic implant 510 is implanted. Accordingly, the opposing forces of the magnetic portions of the first and second endplate components 520 and 540 may be configured to absorb shock, similar to the natural shock absorption of a natural disc. The magnetic portions may also be configured to prevent excess compression, approximation and distraction, in turn, limiting or preventing the creation of wear debris between the first endplate component 520 and the second endplate component 540.

Seventh Exemplary Embodiment

FIGS. 33-37 depict a prosthetic spinal disc in accordance with a seventh embodiment of the present invention. In the illustrated embodiment, the prosthetic spinal disc 610 is comprised of a first (superior) endplate component 620, a second (inferior) endplate component 630, an inferior bearing core 640, a superior bearing core 650, a first flexible connector 660, a second flexible connector 670, and a plurality of set screws 680. With respect to other embodiments, the embodiment illustrated in FIGS. 33-37 is designed with two distinguishing features. First, the flexible connectors 660, 670 do not connect across the endplates 620, 630 from the first lateral edge of the prosthetic spinal disc 610 to the second lateral edge of the prosthetic spinal disc 610. Instead, the first flexible connector 660 connects the endplates 620, 630 along the first lateral edge of the prosthetic spinal disc 610 and the second flexible connector 670 connects the endplates 620, 630 along the second lateral edge of the prosthetic spinal disc 610. Second, the inferior bearing core 640 and the superior bearing core 650 provide the articulating surfaces, while also being secured with set screws 680. The bearing cores 640,650 and the two noted features of the bearing cores 640,650 are distinct from other embodiments described in this specification. In the arrangement provided by this embodiment, the bearing cores 640, 650 are configured to simultaneously provide support, cushioning, and an articulating surface, thereby streamlining the assembly and overall structure and of the implant. In this embodiment, the endplates 620, 630 serve primarily the same function as the endplates of the other embodiments of the invention.

Eighth Exemplary Embodiment

Figure 38:
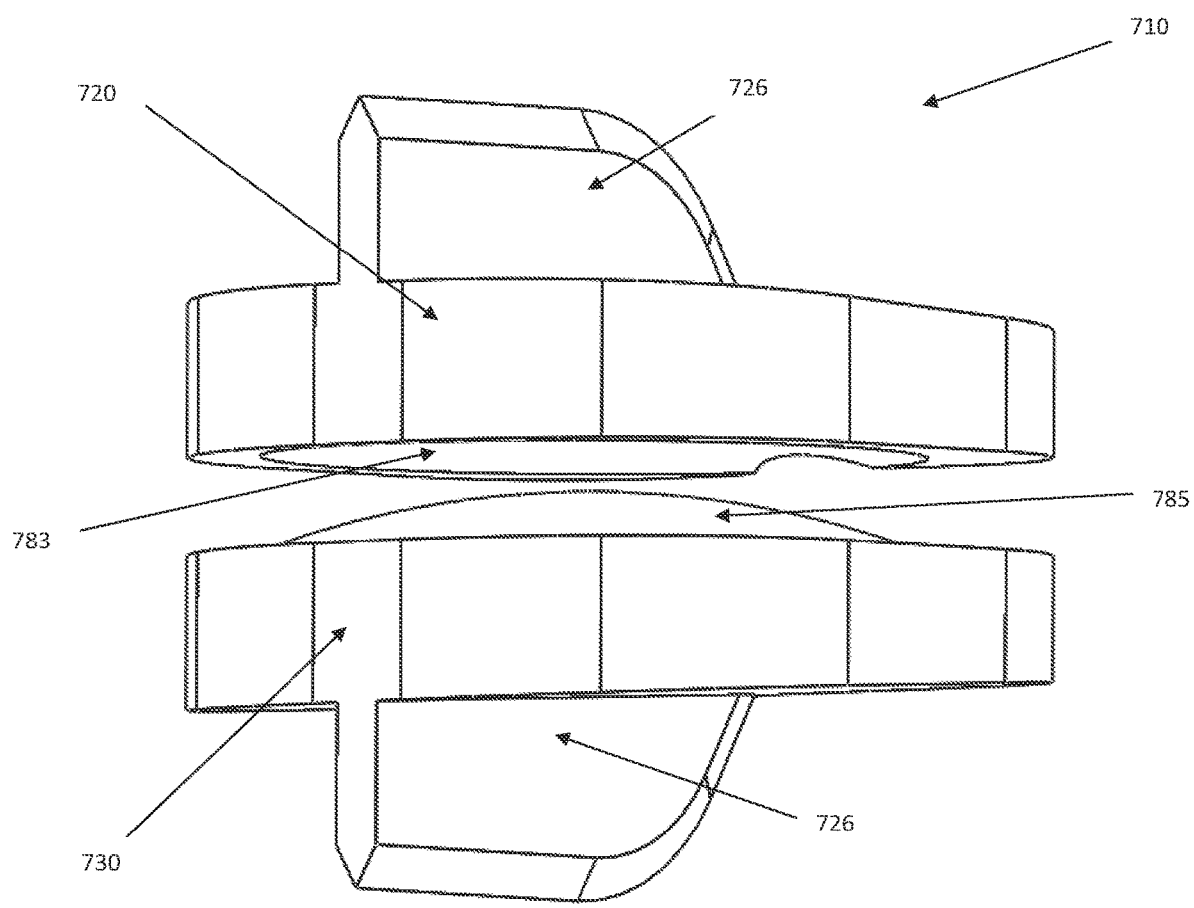
FIG. 38 is a side view of a prosthetic spinal disc in accordance with a eighth embodiment of the present invention.

FIG. 38 is a side view of a prosthetic spinal disc in accordance with a seventh embodiment of the present invention. As shown in FIG. 38, the prosthetic spinal implant 710 may comprise a first endplate component 720 opposing a second endplate component 730. The first and second endplate components 720 and 730 may each be formed partially or substantially from titanium metal. In some embodiments, the first and second endplate components 720 and 730 may be formed from UHMWPE material. The exterior surface of each of the endplate components 720 and 730 may each comprise a vertebral mating surface. As shown in the illustrated example, the vertebral mating surface may comprise one or more keels 726. The first and second endplate components 720 and 730 may each further comprise a magnetic portion. As shown in the depicted example, in some embodiments, the magnetic portion 783 of the first endplate component 720 may be generally concave and the magnetic portion 785 of the second endplate component 730 may be generally convex. In any embodiment, the opposing magnetic portions 783 and 785 of the two endplate components 720 and 730 may create a degree of separation between the two endplate components 720 and 730. In some scenarios, this degree of separation prevents or substantially limits the wear debris that would otherwise be generated by an implanted prosthetic implant 710. In some examples, the magnetic portions 783 and 785 create a de facto cushion or shock absorber to replace the natural shock absorber of the spinal disc which has been removed and replaced by the prosthetic spinal disc 710.

Figure 39A:
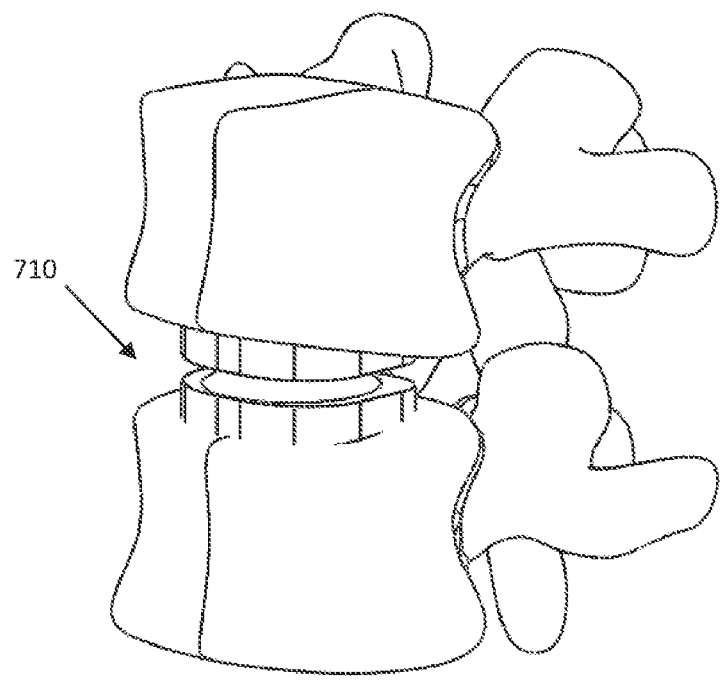
FIG. 39a is a perspective view of a prosthetic spinal disc implanted into a spinal column in accordance with an eighth embodiment of the present invention.
Figure 39B:
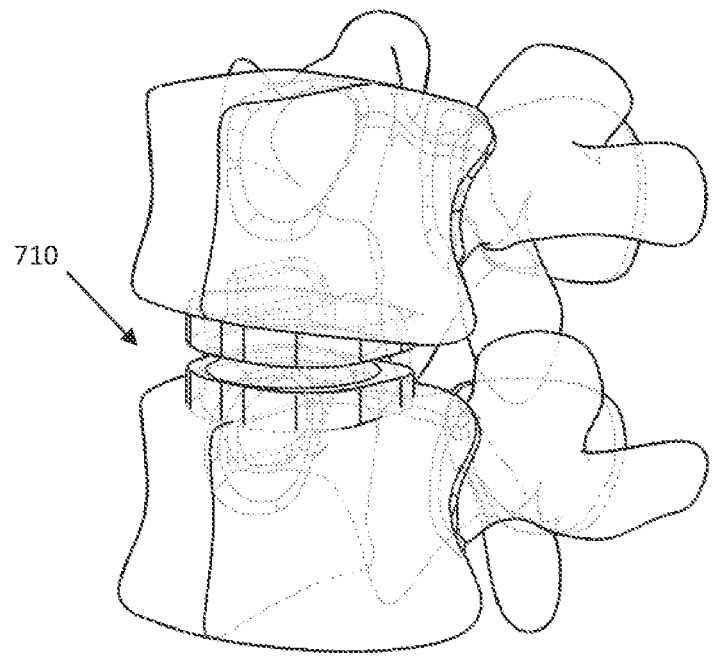
FIG. 39b is a perspective view of a prosthetic spinal disc implanted into a spinal column, where the spinal column is substantially transparent to demonstrate the placement of the prosthetic spinal disc, in accordance with an eighth embodiment of the present invention.
Figure 39C:
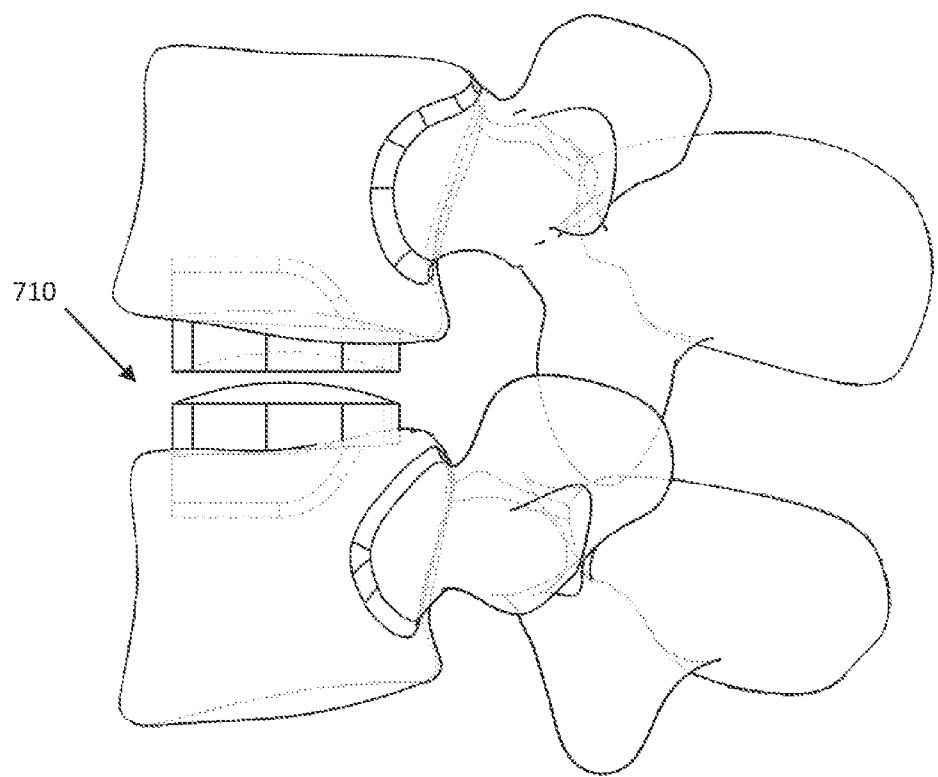
FIG. 39c is a side view of a prosthetic spinal disc implanted into a spinal column, in accordance with an eighth embodiment of the present invention.

FIG. 39a-39c demonstrate exemplary views of a prosthetic spinal disc implanted into a spinal column in accordance with a seventh embodiment of the present invention. As shown in FIGS. 39a-39c, in some embodiments, once implanted, the endplate components 720 and 730 of the prosthetic spinal disc 710 may be configured to not physically touch or otherwise come into contact with one another. Therefore, in some scenarios, little to no wear debris is generated when the implant 710 is in use. This may prevent wear debris from impairing or damaging the implant 710. As further shown in the depicted example, the magnetic portion 783 of the first endplate component 720 may be oriented in a generally exterior position to that of the magnetic portion 785 of the second endplate component 730. Such a configuration may enable the first endplate component 720 to articulate about the second endplate component 730 while containing the second endplate component 730 within a chosen or desired area.

In some scenarios, a spinal disc may be displaced or damaged due to trauma, disease, degenerative defects, or wear over an extended period of time, causing, in some instances, disabling back pain. In some situations, herniated or "slipped" nucleus tissue may apply pressure to spinal nerves, resulting in leg pain, loss of muscle control, or even paralysis. Alternatively, with discal degeneration, the nucleus may lose its water binding ability and deflate, wherein the height of the nucleus decreases, causing the annulus to buckle in areas where laminated plies are loosely bonded. As these overlapping laminated plies of the annulus begin to buckle and separate, either circumferential or radial annular tears may occur, which may contribute to persistent or disabling back pain. Adjacent, ancillary spinal facet joints will also be forced into an overriding position, which may create additional back pain.

Various prior art approaches illustrative of previous attempts to imitate the functions of a normal spinal disc with a disc prosthesis have been developed. The first prosthetics embodied a wide variety of ideas, such as ball bearings, springs, metal spikes and other perceived aids. These prosthetics were all made to replace all or most of the intervertebral disc tissue and are large and rigid. Many of the current designs for prosthetic discs are large, inflexible and provide minimal articulation and fail to incorporate a resistance measure to prevent over-extension or rotation of the device. Moreover, over time, these prior-developed prosthetic disc designs may wear against adjacent vertebral bodies or may themselves generate debris in the disc space. As a result, they may fail to function properly or damage surrounding natural tissue. Additionally, these disc replacements offer little cushioning for axial loads. In some scenarios, excessive shock to the spinal column caused by lack of cushioning may damage other previously healthy portions of the spine.

In various embodiments of the present invention, a prosthetic spinal implant is configured to provide the same articulation as a healthy intervertebral disc. In some examples, the prosthetic spinal disc is configured to replace a damaged disc between two vertebrae of a spine. In some embodiments, the prosthetic spinal implant includes interlocking components which are configured to hold the two endplate components of the implant together and to articulate against one another in order to restore motion to the affected disc space while limiting or altogether preventing the over extension and over rotation of the affected disc space.

The prosthetic spinal implant of the present invention may include interior articulating surfaces, configured to permit the motion of the first and second endplate components relative to one another. In an exemplary embodiment, the articulation function of the prosthetic disc may be configured to allow the disc to rotate axially and radially and allow for flexion, extension and bending of the spine. In some embodiments, the articulation function of the prosthetic disc may be configured to permit movement in one, two, or more than two directions.

In accordance with embodiments of the present invention, the two endplate components of the intervertebral prosthetic disc may each comprise a magnetic portion. In any embodiment, the magnetic portion may be comprised of one or more magnet components.

In accordance with an exemplary embodiment of the present invention, a first endplate component may be configured with a magnetic portion adapted to repel the magnetic portion of a second endplate component. The repelling of the magnetic portions of the two endplate components may enable the first endplate component to articulate about the second endplate component. In some embodiments, one or more connector components, for example, one or more u-shaped elements, may be configured to connect or secure the upper endplate component to the lower endplate component. In any embodiment, the connector components may comprise one or more of the following: u-shaped elements, connector rods, articulating elements, or any other similarly suitable connectors configured to connect the two endplate components and permit their articulation relative to one another.

In an example illustrative of the design and operation of various embodiment implementations, the magnetic portion of the endplate components may be configured to either completely or substantially prevent the two endplate components from coming into direct contact with one another. This reduction or lack of contact between the two endplate components may substantially reduce or altogether prevent the generation of wear debris that may otherwise be problematic if the two endplate components were to come into contact or rub against one another. Such a configuration may also prevent wear debris from impairing, damaging or adversely affecting the device, surrounding tissue, or nearby bone. Additionally, the magnetic portions of the endplate components may cause the two endplate components to repel one another such that a cushioning effect is generated in the spine, to mimic the movement of a natural disc.

In another example illustrative of the design and operation of various embodiment implementations, the magnetic portions of each of the endplate components may be configured to repel as well as contain the magnetic portion of the other endplate component. For example, a magnetic portion of a first endplate component may be configured to repel and contain a magnetic portion of a second endplate component. In some examples, the magnetic portion of the first endplate component may be oriented in a generally exterior position to that of the magnetic portion of the second endplate component. Such a configuration may enable the first endplate component to articulate about the second endplate component while containing the second endplate component within a chosen or desired area.

In any embodiment, the magnet components may be temporary magnets or permanent magnets. Further, one or more of the magnet components contemplated herein may be neodymium iron boron (NdFeB), samarium cobalt (SmCo), alnico, and ceramic or ferrite magnets. One of ordinary skill in the art would appreciate that there are numerous suitable and advantageous magnet configurations depending on the specific intended use application of the particular prosthetic spinal disc and embodiments of the present invention are contemplated for use with any such magnet configurations.

In any embodiment, the magnet components are contemplated to have the orientation of any geometric shape, including: squares, rectangles, circles, ovals, pentagons, hexagons, triangles. In some embodiments, the magnet components may have concave or convex portions. One of ordinary skill in the art would appreciate that there are numerous suitable and advantageous arrangements for the geometric orientation of the magnet components depending on the specific intended use application of the particular prosthetic spinal disc and embodiments of the present invention are contemplated for use with any such magnet components.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments. elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of." In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f).

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

The invention claimed is:

1. A prosthetic spinal implant configured to articulate in at least two planes, comprising:
   a pair of endplate components operably connected to form an articulating joint, wherein each endplate component comprises a base and an exterior surface adapted to engage with bone;
   a first flexible connector attaching between the pair of end plate components at a first lateral edge of the prosthetic spinal implant;
   a second flexible connector attaching between the pair of end plate components at a second lateral edge of the prosthetic spinal implant; and
   a connector receiving opening entirely set in from a boundary of each lateral edge of a first endplate of the pair of endplates, each of the connector receiving openings comprising,
      a connector slot formed in the exterior surface of the first endplate, and
      a first connector hole and a second connector hole formed in the base of the first endplate, wherein the first connector hole and the second connector hole are separated by a portion of the base.

2. The prosthetic spinal implant of claim 1, further comprising a pair of connector holes formed along each lateral edge of a second endplate of the pair of endplate components, wherein a first end of the flexible connector is fully enclosed by a first connector hole of the pair of connector holes and a second end of the flexible connector is fully enclosed by a second connector hole of the pair of connector holes.

3. The prosthetic spinal implant of claim 1, wherein the connector slot enables each of the flexible connectors to be retained below the exterior surface of the first endplate.

4. The prosthetic spinal implant of claim 1, wherein each of the flexible connectors is received within one of the connector receiving openings by looping over and abutting with the portion of the base separating the first and second connector holes.

5. The prosthetic spinal implant of claim 1, further comprising a bearing core attached to the base of each of the endplates components, wherein each bearing core is attached to the base with a fastener.

6. The prosthetic spinal implant of claim 5, wherein each bearing core has an interior face configured to attach to the base of the endplate component and an exterior face formed with an articulation surface.

7. The prosthetic spinal implant of claim 5, wherein each bearing core is attached to the base of the endplate component between the first flexible connector and the second flexible connector.

8. A prosthetic spinal implant, comprising:
   a first endplate component and a second endplate component that are operably connected to form an articulating joint, wherein each endplate component comprises a base and an exterior surface adapted to engage with bone;
   a first connector slot formed along and entirely set in from a boundary of a first lateral edge of the second endplate component;
   a second connector slot formed along and entirely set in from a boundary of a second lateral edge of the second endplate component;
   a first flexible connector attaching the first and second endplate components at the first lateral edge of the prosthetic spinal implant, wherein a portion of the first flexible connector loops through a pair of connector holes formed in the first connector slot and the first connector slot encircles the portion of the first flexible connector looping through the first connector slot; and
   a second flexible connector attaching the first and second endplate components at the second lateral edge of the prosthetic spinal implant, wherein a portion of the second flexible connector loops through a pair of connector holes formed in the second connector slot and the second connector slot encircles the portion of the second flexible connector looping through the second connector slot.

9. The prosthetic spinal implant of claim 8, further comprising a bearing core attached to each of the endplates components.

10. The prosthetic spinal implant of claim 9, wherein each bearing core has an interior face configured to attach to the endplate component and an exterior face formed with an articulation surface configured to enable each of the bearing cores to pivot against the other.

11. The prosthetic spinal implant of claim 8, wherein the first flexible connector and the second flexible connector are not fastened to the second endplate with a fastener.

12. A prosthetic spinal implant, comprising:
   a first endplate component and a second endplate component that are operably connected to form an articulating joint, wherein each endplate component comprises a base and an exterior surface adapted to engage with bone;
   a first connector slot formed along and entirely set in from a boundary of a first lateral edge of the second endplate component;
   a second connector slot formed along and entirely set in from a boundary of a second lateral edge of the second endplate component;
   first flexible connector attaching the first and second endplate components at the first lateral edge of the prosthetic spinal implant, wherein a portion of the first flexible connector loops through a pair of connector holes formed in the first connector slot and the first connector slot encircles the portion of the first flexible connector looping through the first connector slot;
   a second flexible connector attaching the first and second endplate components at the second lateral edge of the prosthetic spinal implant, wherein a portion of the second flexible connector loops through a pair of connector holes formed in the second connector slot and the second connector slot encircles the portion of the second flexible connector looping through the second connector slot; and
   a bearing core attached to each of the endplate components by one or more fasteners, wherein each bearing core has an interior face configured to attach to the endplate component and an exterior face formed with an articulation surface configured to enable each of the bearing cores to pivot against the other;
   wherein the bearing core of the first endplate component is configured as an elongate convex ramp, and the bearing core of the second endplate component is configured as a corresponding elongate concave groove.

13. The prosthetic spinal implant of claim 8, wherein each of the connector slots forms an enclosed border within which the portion of the flexible connector is retained to prevent the flexible connector from exiting the connector slot.

14. The prosthetic spinal implant of claim 10, wherein a first bearing is core configured as a ramp with its articulation surface having an elongate convex profile and second bearing core is configured as a groove with an elongate concave profile that corresponds to the first bearing core.

15. The prosthetic spinal implant of claim 12, wherein the bearing cores correspond in shape to each other to interlock and limit axial rotation of the endplate components with respect to one another.

16. The prosthetic spinal implant of claim 12, wherein the bearing cores and their respective articulating surfaces are configured to limit axial rotation of the endplate components with respect to each other.

\* \* \* \* \*